United States Patent
Tajima

(10) Patent No.: US 10,123,757 B2
(45) Date of Patent: Nov. 13, 2018

(54) IMAGE-PROCESSING DEVICE, RADIATION IMAGE CAPTURE SYSTEM, IMAGE-PROCESSING METHOD, AND COMPUTER-READABLE STORAGE MEDIUM

(71) Applicant: FUJIFILM CORPORATION, Minato-ku, Tokyo (JP)

(72) Inventor: Takashi Tajima, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 60 days.

(21) Appl. No.: 15/375,179

(22) Filed: Dec. 12, 2016

(65) Prior Publication Data
US 2017/0273649 A1   Sep. 28, 2017

(30) Foreign Application Priority Data
Mar. 22, 2016   (JP) .................... 2016-057640

(51) Int. Cl.
*G06K 9/00* (2006.01)
*A61B 6/00* (2006.01)
*G06T 5/00* (2006.01)

(52) U.S. Cl.
CPC .............. *A61B 6/50* (2013.01); *A61B 6/5217* (2013.01); *A61B 6/5282* (2013.01); *G06T 5/006* (2013.01); *A61B 6/461* (2013.01); *G06T 2200/32* (2013.01); *G06T 2207/10116* (2013.01); *G06T 2207/20012* (2013.01); *G06T 2207/30004* (2013.01)

(58) Field of Classification Search
CPC ......... A61B 6/461; A61B 6/50; A61B 6/5217; A61B 6/5282; G06T 2200/32; G06T 2207/10116; G06T 2207/20012; G06T 2207/30004; G06T 5/006
See application file for complete search history.

(56) References Cited

U.S. PATENT DOCUMENTS

| | | | |
|---|---|---|---|
| 8,768,026 B2* | 7/2014 | Ren ...................... | A61B 6/0414 382/131 |
| 2001/0038707 A1* | 11/2001 | Ohara .................. | A61B 6/4233 382/132 |
| 2002/0081010 A1* | 6/2002 | Chang .................. | A61B 6/5241 382/132 |

(Continued)

FOREIGN PATENT DOCUMENTS

| JP | H03-244440 A | 10/1991 |
|---|---|---|
| JP | 2013-198736 A | 10/2013 |

*Primary Examiner* — Brian Werner
*Assistant Examiner* — Ian L Lemieux
(74) *Attorney, Agent, or Firm* — SOLARIS Intellectual Property Group, PLLC

(57) ABSTRACT

An overall controller of a console acquires a radiation image of an imaging subject captured by a radiation image capture device for radiographic imaging. The overall controller also acquires body thickness information indicating a body thickness of the imaging subject in a direction in which radiation passes through. The overall controller also adds to the radiation image an assist line image that have would be expected to be obtained if a predetermined member had been disposed and captured at a position inside the imaging subject determined based on the acquired body thickness information, or at a position between the imaging subject and the radiation image capture device.

12 Claims, 15 Drawing Sheets

(56) References Cited

U.S. PATENT DOCUMENTS

| | | | | |
|---|---|---|---|---|
| 2008/0152088 A1* | 6/2008 | Wang | ............... | A61B 6/02 |
| | | | | 378/98.12 |
| 2012/0076262 A1* | 3/2012 | Tajima | ............... | A61B 6/022 |
| | | | | 378/41 |
| 2012/0157819 A1* | 6/2012 | Jerebko | ............... | A61B 6/502 |
| | | | | 600/407 |
| 2014/0363071 A1* | 12/2014 | Imai | ............... | A61B 6/4291 |
| | | | | 382/132 |

* cited by examiner

LATTICE FORM
ASSIST LINES

GRADUATED (CM) LATTICE
FORM ASSIST LINES

GRADUATED (INCH) LATTICE
FORM ASSIST LINES

GRADUATED
ASSIST LINE

STRAIGHT-LINE FORM
ASSIST LINES

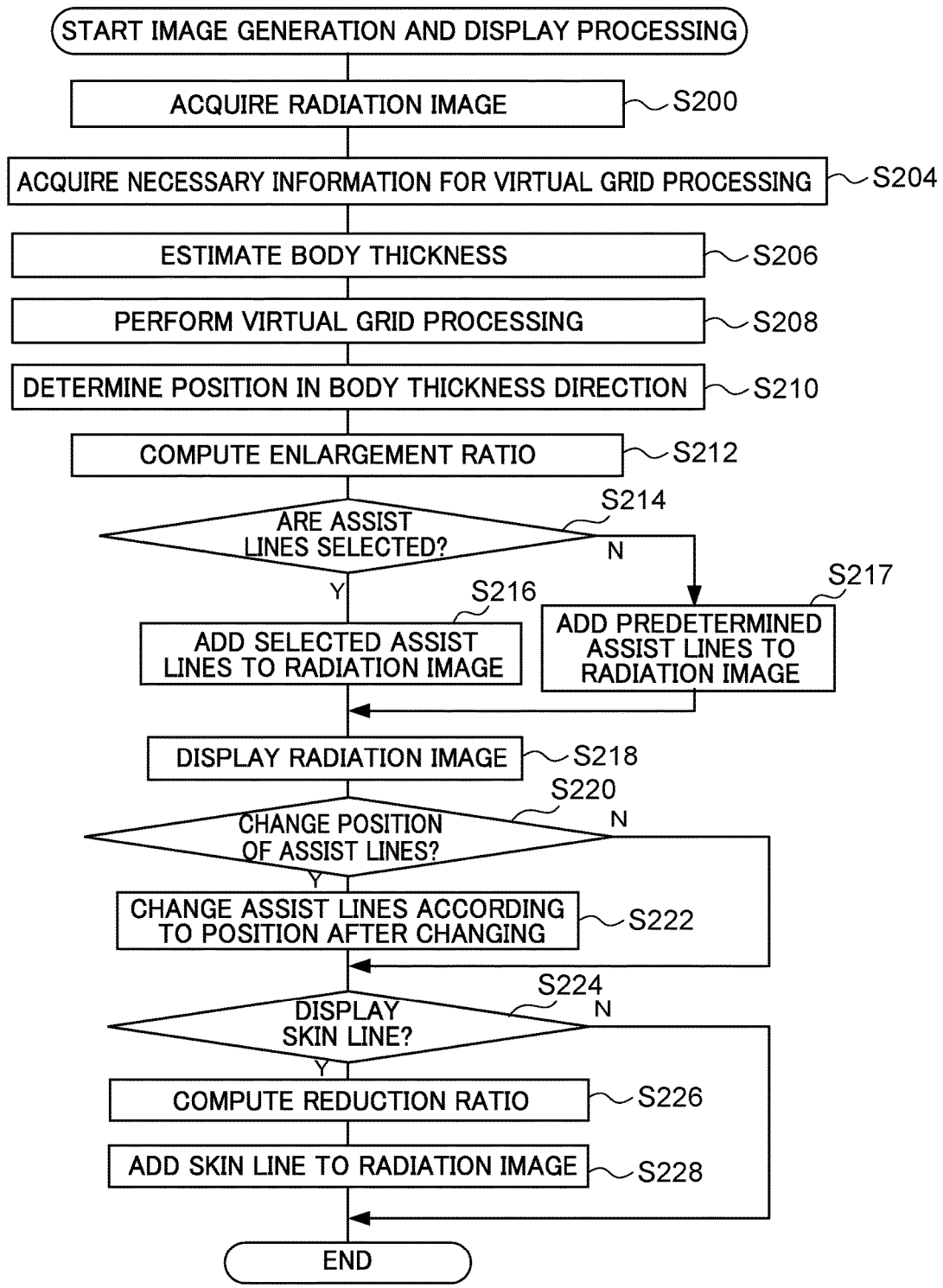

IMAGE-PROCESSING DEVICE, RADIATION IMAGE CAPTURE SYSTEM, IMAGE-PROCESSING METHOD, AND COMPUTER-READABLE STORAGE MEDIUM

CROSS-REFERENCE TO RELATED APPLICATIONS

The present application claims priority under 35 U.S.C § 119 to Japanese Patent Application No. 2016-057640, filed on Mar. 22, 2016, which is hereby expressly incorporated by reference, in its entirety, into the present application.

BACKGROUND

Technical Field

The present disclosure relates to an image-processing device, a radiation image capture system, an image-processing method, and a computer-readable storage medium.

Related Art

Radiation image capture systems are known in which capture of a radiation image of an imaging subject is performed by a radiation image capture device detecting radiation that has been emitted from a radiation radiating device and has passed through the imaging subject using a radiation detector.

In this type of radiation image capture system, for radiation images that image a site of interest of an imaging subject, assist lines are sometimes added to the radiation image in order to assist observation of the site of interest.

Technology in which a plate, formed with a metal lattice form pattern for adding assist lines, is provided between the imaging subject and the radiation image capture device, and the lattice form pattern is imprinted as a ghost image onto the radiation image, for example, is known as technology to add assist lines to the radiation image.

Technology is also known, for example, in which lattice form assist lines generated by executing software processing or the like are added to a radiation image and displayed instead of imaging employing an actual plate for adding assist lines (see Japanese Patent Application Laid-Open (JP-A) Nos. 2013-198736 (Patent Document 1) and H03-244440 (Patent Document 2)).

However, in actual plates for adding assist lines, for example, lattice form grooves are made in an acrylic base, and a material such as metal with strong radiation shielding properties is provided inside the formed grooves. Thus, in cases in which an actual plate for adding assist lines is employed in imaging, the plate for adding assist lines has a comparatively heavy weight, and so sometimes cannot be easily installed. It is also not easy to install the plate for adding assist lines in a position where the assist lines are imprinted as a ghost image in a suitable position on the radiation image. Thus, in cases in which an actual plate for adding assist lines is employed in imaging, there is a burden on an operator such as a doctor or a technician, and so it is desirable to lighten the burden on the operator by improving the work procedure of the operator.

In the technology of Patent Documents 1 and 2, assist lines are generated by executing software processing or the like; however, the position of the assist lines are predetermined regardless of the site of interest to be observed by a doctor reading the radiation image, such that there is a concern that the assist lines might interfere with the site of interest, hinder the reading by the doctor, and prevent a diagnosis.

SUMMARY

An object of the embodiments of the present invention is to provide an image-processing device capable of displaying an assist line for assisting observation of a site of interest in a suitable position in a radiation image, and a radiation image capture system, an image-processing method, and a computer-readable storage medium of the same.

An image-processing device according to an aspect of the present invention includes a processor, the processor being configured to: acquire a radiation image of an imaging subject captured by a radiation image capture device for radiographic imaging; acquire body thickness information indicating a body thickness of the imaging subject in a direction in which radiation passes through; and add to the radiation image an assist line image that would be expected to be obtained if a predetermined member had been disposed and captured at a position inside the imaging subject determined based on the body thickness information, or at a position between the imaging subject and the radiation image capture device.

An image-processing method according to an aspect of the present invention is a method including causing a computer to execute processing including: acquiring a radiation image of an imaging subject captured by a radiation image capture device for radiographic imaging; acquiring body thickness information indicating a body thickness of the imaging subject in a direction in which radiation passes through; and adding to the radiation image an assist line image that would be expected to be obtained if a predetermined member had been disposed and captured at a position inside the imaging subject determined based on the acquired body thickness information, or at a position between the imaging subject and the radiation image capture device.

A non-transitory computer-readable storage medium according to an aspect of the present invention is stored with an image-processing program executable by a computer to perform processing including: acquiring a radiation image of an imaging subject captured by a radiation image capture device for radiographic imaging; acquiring body thickness information indicating a body thickness of the imaging subject in a direction in which radiation passes through; and adding to the radiation image an assist line image that would be expected to be obtained if a predetermined member had been disposed and captured at a position inside the imaging subject determined based on the acquired body thickness information, or at a position between the imaging subject and the radiation image capture device.

BRIEF DESCRIPTION OF THE DRAWINGS

An exemplary embodiment of the present invention will be described in detail based on the following figures, wherein:

FIG. 13 is a flowchart illustrating a flow of image generation and display processing executed by the console illustrated in FIGS. 11 and 12.

DETAILED DESCRIPTION

Detailed explanation follows regarding an exemplary embodiment of the present invention, with reference to the drawings. Note that the present invention is not limited to the present exemplary embodiment.

Figure 1:
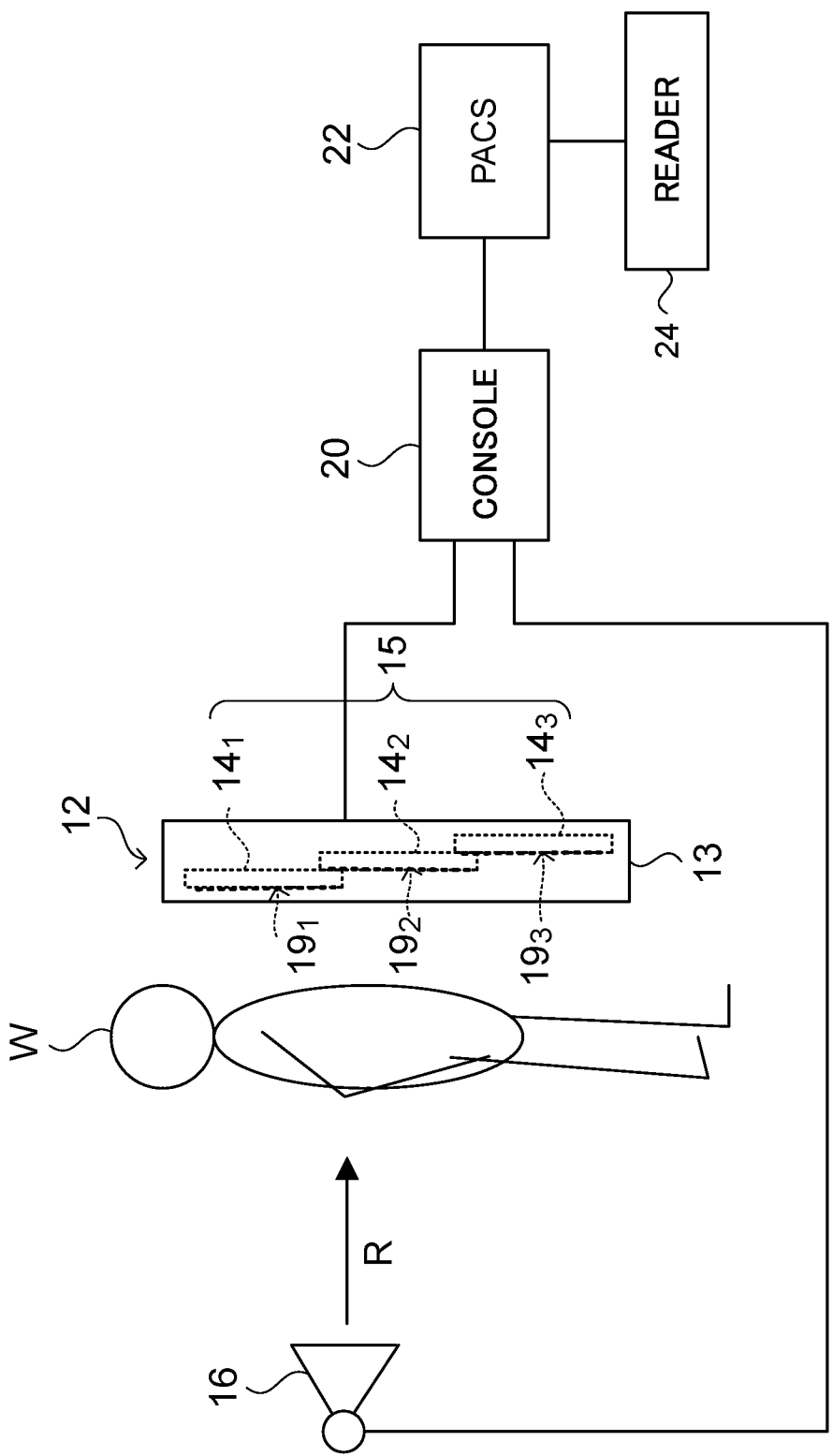
FIG. 1 is a configuration diagram illustrating a configuration of a radiation image capture system of an exemplary embodiment.
Figure 2:
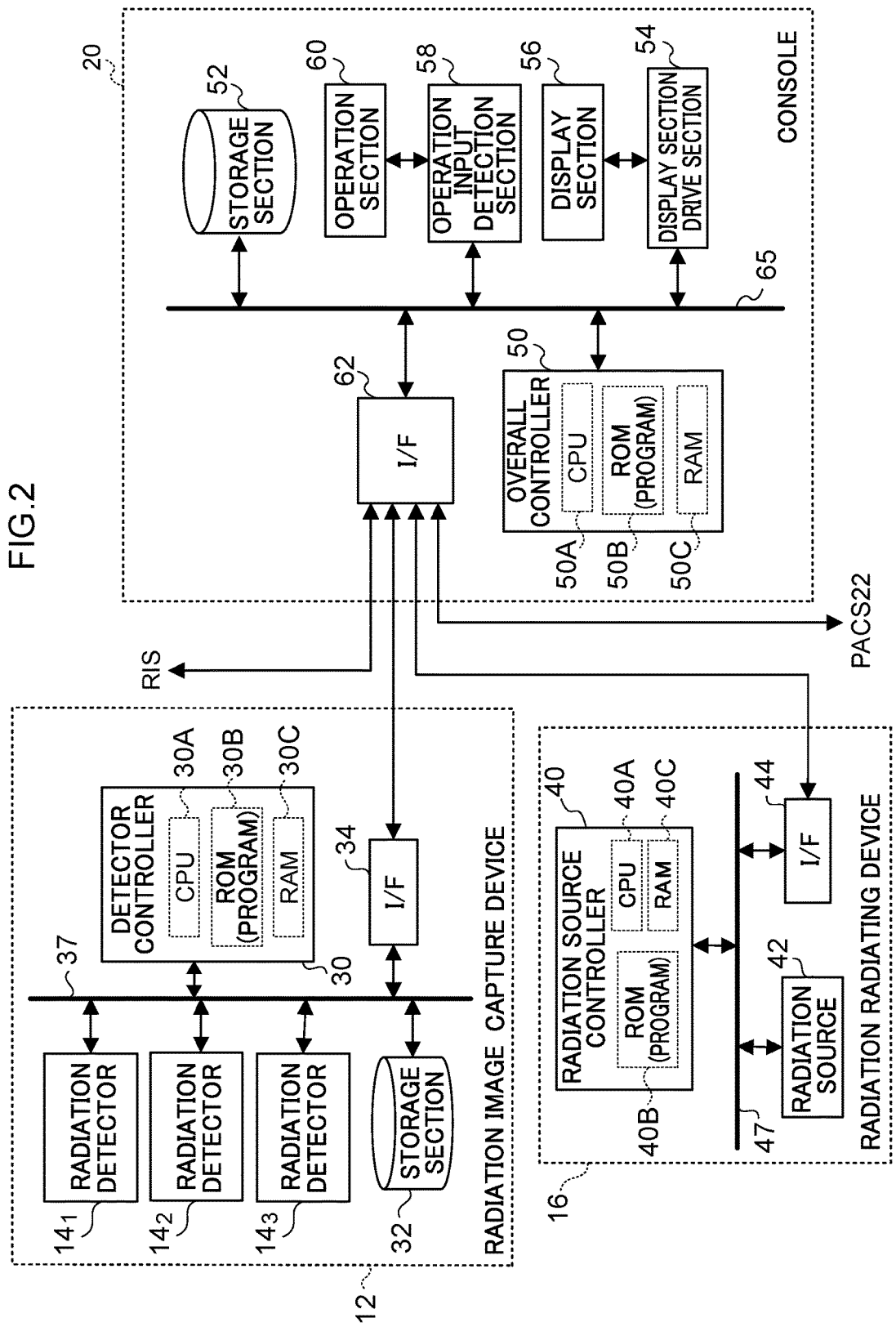
FIG. 2 is a block diagram illustrating a configuration of the radiation image capture system of the present exemplary embodiment illustrated in FIG. 1.

First, explanation follows regarding a configuration of a radiation image capture system of the present exemplary embodiment, with reference to FIG. 1 and FIG. 2.

As illustrated in FIG. 1, a radiation image capture system 10 of the present exemplary embodiment includes a radiation image capture device 12, a radiation radiating device 16, and a console 20. The radiation image capture system 10 of the present exemplary embodiment is operated by an operator to capture a radiation image based on an imaging menu acquired by the console 20 from an external system such as a radiology information system (RIS), an imaging menu input by the operator, or the like.

As illustrated in FIG. 2, the radiation radiating device 16 of the present exemplary embodiment includes a radiation source controller 40, a radiation source 42, and an interface (I/F) 44. The radiation source controller 40, the radiation source 42, and the I/F 44 are connected together by a bus 47, such as a system bus or a control bus, so as to be capable of exchanging information and the like with each other. The radiation radiating device 16 radiates radiation R from the radiation source 42 onto an imaging site (such as the chest or lumbar region) of an imaging subject W under the control of the console 20.

The radiation source 42 includes a vacuum tube (not illustrated in the drawings) and emits the radiation R under the control of the radiation source controller 40. In the below explanation, the position of the vacuum tube is the same as the position of the radiation source 42.

The radiation source controller 40 controls the radiation source 42 based on radiation conditions of the radiation R, such as tube voltage, tube current, and radiation duration. The radiation source controller 40 includes a central processing unit (CPU) 40A, read only memory (ROM) 40B, and random access memory (RAM) 40C. Programs, etc. to be executed by the CPU 40A are pre-stored in the ROM 40B. The radiation radiating device 16 performs control relating to the radiation R emitted from the radiation source 42 by the CPU 40A executing a program stored in the ROM 40B. The RAM 40C temporarily stores various data. Note that CPU 40A may be configured as, but not limited to, a processor, a hardware processor, a processing circuit, or a processing circuitry.

The I/F 44 exchanges various information with the console 20 by wireless communication, wired communication, or the like.

Note that the radiation radiating device 16 may also include an operation input section in order for the operator to manually set the radiation conditions directly to the radiation radiating device 16, and a display section for displaying the set radiation conditions and so on. When the radiation conditions have been manually set by the operator, the radiation radiating device 16 transmits information expressing setting values that have been manually set, the current status (such as a standby state, a preparatory state, an exposure in-progress state, or an exposure complete state), and so on to the console 20.

The radiation image capture device 12 of the present exemplary embodiment is what is referred to as an long-length imaging digital radiography (DR) cassette. "Long-length imaging" refers to capturing a comparatively long site on the imaging subject W, such as the entire spine or the entire lower limbs. Although "employed for long-length imaging" refers to being employed in long-length imaging, it is not dedicated to long-length imaging, and may be employed in imaging that is not long-length imaging, such as of the chest or head.

As illustrated in the example in FIG. 1, the radiation image capture device 12 of the present exemplary embodiment includes a radiation detector group 15 inside a casing 13, and the radiation detector group 15 includes three radiation detectors $14_1$ to $14_3$. When referred to collectively below, the numeral suffix denoting each individual detector is omitted, and the radiation detectors $14_1$ to $14_3$ are referred to as "radiation detectors 14". Note that the number of radiation detectors 14 is not limited to the number in the present exemplary embodiment.

When capturing a radiation image, a radiation image is captured by all the radiation detectors 14 by emitting radiation R a single time (what is referred to as one shot).

The radiation detectors 14 of the present exemplary embodiment are disposed in a state in which detection faces $19_1$ to $19_3$ (regions of pixels (not illustrated in the drawings) effective for imaging) face the imaging subject W. When referred to collectively below, the final reference numeral denoting each detection face is omitted, and the detection faces $19_1$ to $19_3$ are referred to as "detection faces 19". Note that, as illustrated in FIG. 1, an end portion of each radiation detector 14 is disposed overlapping an end portion of an adjacent radiation detector 14 in the radiation image capture device 12 of the present exemplary embodiment.

When there is a spacing separating the end portions of adjacent radiation detectors 14 there are sometimes parts of the imaging site of the imaging subject W that are not captured, and it is also sometimes difficult to dispose the end portions of adjacent radiation detectors 14 in close contact with each other without any gaps therebetween, due to manufacturing variations in the radiation detectors 14. Thus, as illustrated in FIG. 1, the end portion of the detection face 19 of a radiation detector 14 and the end portion of the detection face 19 of an adjacent radiation detector 14 are disposed overlapping each other in the radiation detector group 15 of the radiation image capture device 12 of the present exemplary embodiment. Specifically, the detection faces 19 at the end portions of adjacent radiation detectors 14 are overlapped in the direction of incidence of the radiation R. Note that the range (size) of the detection face 19 at overlapping portions where the radiation detectors 14 overlap each other is predetermined according to the degree at which the radiation R radiated from the radiation radiating device 16 is obliquely incident (incident at an incline), and so on.

Since the radiation image capture device 12 of the present exemplary embodiment includes the plural radiation detectors 14 disposed in the above manner, the whole of the radiation image capture device 12 has a longer length detection face than the detection face 19 of just one radiation detector 14.

Radiation R that has passed through the imaging subject W is radiated onto the radiation detectors 14 of the radiation image capture device 12. Each radiation detector 14 of the radiation image capture device 12 generates charge according to the dose of radiation R that has passed through the imaging subject W, and generates and outputs image data of a radiation image (hereafter simply referred to as "radiation image") based on the amount of generated charge.

As illustrated in FIG. 2, the radiation image capture device 12 of the present exemplary embodiment also includes a detector controller 30, a storage section 32, and an I/F 34. The detector controller 30, the radiation detectors $14_1$ to $14_3$, the storage section 32, and the I/F 34 are connected together by a bus 37, such as a system bus or a control bus, so as to be capable of exchanging information and the like with each other.

The detector controller 30 controls the radiation image capture device 12 as a whole. As illustrated in FIG. 2, the detector controller 30 of the present exemplary embodiment includes a CPU 30A, ROM 30B, and RAM 30C. Programs, etc. to be executed by the CPU 30A are pre-stored in the ROM 30B. The radiation image capture device 12 controls the radiation detectors 14 by the CPU 30A executing a program stored in the ROM 30B. Note that CPU 30A may be configured as, but not limited to, a processor, a hardware processor, a processing circuit, or a processing circuitry.

The storage section 32 stores radiation images and the like captured by the radiation detectors 14.

The I/F 34 exchanges various information with the console 20 by wireless communication, wired communication, or the like.

In the present exemplary embodiment, radiation images captured by the radiation image capture device 12 are input to the console 20 through the I/F 34.

The console 20 of the present exemplary embodiment is a server computer. As illustrated in FIG. 2, the console 20 of the present exemplary embodiment includes an overall controller 50, a storage section 52, a display section drive section 54, a display section 56, an operation input detection section 58, an operation section 60, and an I/F 62. The overall controller 50, the storage section 52, the display section drive section 54, the display section 56, the operation input detection section 58, the operation section 60, and the I/F 62 are connected together by a bus 65, such as a system bus or a control bus, so as to be capable of exchanging information and the like with each other. In the present exemplary embodiment, the console 20 functions as an image-processing device.

The console 20 transmits at least one from out of radiation images that have been image-processed (described in detail later) by the overall controller 50, or radiation images (prior to image-processing) as acquired from the radiation image capture device 12, to a picture archiving and communication system (PACS) 22. The PACS 22 manages radiation images received from the console 20. The radiation images managed by the PACS 22 are displayed on at least one out of a display section (not illustrated in the drawings) of a reader 24 or the display section 56 of the console 20, according to an instruction from a doctor reading the radiation images, for example. Note that the reader 24 is a device employed in order to read the captured radiation images. There is no particular limitation thereto, and examples include what is referred to as a viewer, as well as personal digital assistants (PDAs) such as personal computers, tablet terminals, and smartphones employed by a doctor.

The overall controller 50 controls overall operation of the console 20. As illustrated in FIG. 2, the overall controller 50 includes a CPU 50A, ROM 50B, and RAM 50C. Various programs, etc. to be executed by the CPU 50A are pre-stored in the ROM 50B. The RAM 50C temporarily stores various data. Note that CPU 50A may be configured as, but not limited to, a processor, a hardware processor, a processing circuit, or a processing circuitry.

The overall controller 50 of the console 20 of the present exemplary embodiment controls the radiation image capture device 12 and the radiation radiating device 16 using an imaging menu and various other information acquired, for example, from an external system by wireless communication. The overall controller 50 of the console 20 performs plural types of predetermined image-processing on radiation images acquired from the radiation image capture device 12. Explanation follows regarding the image-processing executed by the overall controller 50 of the present exemplary embodiment.

As described above, the radiation image capture device 12 of the present exemplary embodiment captures images using the radiation detectors 14 which are overlapped in what is referred to as a stepped pattern. A radiation image is captured by each of the three radiation detectors 14, and so the overall controller 50 performs image-processing by stitching together the radiation images captured by each radiation detector 14 (hereafter referred to as "stitching processing") to obtain a long-length radiation image using the whole of the radiation image capture device 12.

For overlapping radiation detectors 14, a shadow of the radiation detector 14 nearer to the radiation radiating device 16 is sometimes imprinted as an image of the step onto the radiation image captured by the radiation detector 14 further from the radiation radiating device 16. For example, in the case illustrated in FIG. 1, an end portion of the radiation detector $14_1$ is imprinted as a step image onto the radiation image captured by the radiation detector $14_2$, and an end portion of the radiation detector $14_2$ is imprinted as a step image onto the radiation image captured by the radiation detector $14_3$. The overall controller 50 therefore performs image-processing to remove the step image from each radiation image (hereafter referred to as "step removal processing").

Note that there is no particular limitation to the respective image-processing methods for stitching processing and step removal processing. For example, step removal processing may be performed in the below manner.

A step image is included in the radiation image captured by the respective radiation detector 14 that is further from the radiation radiating device 16, and so the step removal processing of the present exemplary embodiment is performed on the radiation image captured by the respective radiation detector 14 further from the radiation radiating device 16. There is no particular limitation to the method by which the overall controller 50 recognizes whether a radiation image acquired from the radiation detector group 15 has been captured by a radiation detector 14 further from the radiation radiating device 16, or by a radiation detector 14 nearer thereto. For example, information indicating whether each radiation detector 14 is a radiation detector 14 further away or nearer than an adjacent radiation detector 14 may be added to the radiation image and output to the console 20.

When correcting a step image, the overall controller 50 first detects the position of the step image in the radiation image. There is no particular limitation to the detection method of the position of the step image. As a specific example, the overall controller 50 of the present exemplary embodiment detects the position of a boundary between the step image and the normal image by detecting an image expressing a straight line in the radiation image, and detects the position of the step image based on the detected position of the boundary. Note that the boundary between the step image and the normal image is simply referred to below as "boundary". There is no particular limitation to the method of detecting a straight line, and a general method, such as the Hough transform, may be employed. There is also no particular limitation to the method of detecting the position of a step image from the position of the boundary, and, for example, the region between the position of the boundary and a specific end portion of the radiation image may be detected as the step image.

When detecting the position of the boundary in the radiation image, processing to detect the position of the boundary may be performed on the entire radiation image, or may be performed by searching within a search range, this search range being a region in which the position of the boundary is estimated to be contained. For example, a possible range within which the position of the step image (the position of the boundary) may lie in the radiation image may be obtained based on the design or by experimentation, and this range applied as the search range. Detecting the position of the boundary within the estimated search range enables the detection accuracy to be improved and also enables the detection duration to be reduced, compared to cases in which the position of the boundary is detected from the entire radiation image.

When the position of the step image is detected, the overall controller 50 then corrects the step image included in the radiation image. The overall controller 50 of the present exemplary embodiment corrects the step image by correcting to reduce a difference in density between the density of the step image and the density of the normal image. Note that the step correction can be more accurately performed by performing offset correction, gain correction, pixel defect correction, and the like on the radiation image prior to correcting to reduce the difference in density.

The overall controller 50 of the present exemplary embodiment also performs virtual grid processing as image-processing. Generally, when capturing a radiation image, scattered radiation is generated due to the radiation R passing through the imaging subject W, and so scattered radiation is included in the radiation R that has passed through the imaging subject W. Thus, the scattered radiation included in the radiation R reaching the radiation detectors 14 is removed by providing a grid between the imaging subject W and the radiation detectors 14 to remove the scattered radiation. Advantageous effects are obtained by removing the scattered radiation, such as suppressing a reduction in the contrast of the radiation image, thereby improving the quality of the radiation image. In the radiation image capture system 10 of the present exemplary embodiment, virtual grid processing is performed by the overall controller 50 of the console 20 to remove the influence of scattered radiation, based on the properties of a virtually applied virtual grid, without using an actual grid.

There is no particular limitation to the method of virtual grid processing. For example, the technology described in JP-A No. 2015-192846 may be applied. When applying the technology described in JP-A No. 2015-192846 to the present exemplary embodiment, first, the overall controller 50 acquires imaging conditions such as the tube voltage of the radiation source 42, and the dose of radiation R radiated toward the imaging subject W (the product of tube current and radiation duration, referred to as an mAs value). Based on the acquired imaging conditions, the overall controller 50 then derives the properties of a grid virtually applied to remove scattered radiation in radiation images, as virtual grid properties to set a scattered radiation removal amount. Note that the virtual grid properties are predetermined according to the type of virtual grid. Examples of the virtual grid properties include a grid ratio of the virtual grid. Generally, thin strips of lead having a high radiation R absorption ratio, and a substance having a low radiation R absorption ratio and serving as an intermediate substance (interspaces) between the thin lead strips, are disposed alternately to each other with a fine lattice density, such as approximately 4.0 strips/mm. Aluminum, paper, or carbon fibers, for example, may be employed as the material of the intermediate substance. The grid ratio is defined as the height ratio of the lead, taking the distance between strips of lead (the thickness of the intermediate substance) as "1". A high grid ratio is effective in reducing scattered radiation and increases the amount of scattered radiation removed. Generally, the higher the tube voltage of the radiation source 42 (the higher the radiation R energy) used, the greater the scattered radiation, and so a higher grid ratio is employed. The virtual grid properties may also include such factors as the grid density (lattice density), whether the strips converge or are parallel to each other, the focal distance if the strips converge, and the material of the intermediate substance. The overall controller 50 executes virtual grid processing on the radiation image using a removal amount based on the derived virtual grid properties.

The overall controller 50 of the present exemplary embodiment also performs image-processing (described in detail later) to add to the radiation image an assist line image that would be expected to be obtained if a predetermined member had been disposed and captured at a position inside the imaging subject W determined based on the body thickness of the imaging subject W (the thickness in a direction in which the radiation R passes through).

The display section drive section 54 illustrated in FIG. 2 controls the display of various information on the display section 56. The display section 56 displays an imaging menu, radiation images that have been captured, and so on. The operation input detection section 58 detects an operation state of the operation section 60 by the operator. The operation section 60 is used by a doctor to input instruction operations for capturing a radiation image, instructions relating to image-processing of captured radiation images, and so on. The operation section 60 may take the form of a keyboard, for example, or may take the form of a touch panel that is integrated with the display section 56.

The I/F 62 exchanges various information between the PACS 22 and the RIS by wireless communication or the like. The I/F 62 also exchanges various information between the radiation image capture device 12 and the radiation radiating device 16. The storage section 52 stores and retains radiation images and various other data.

Explanation follows regarding an operation when a radiation image is captured by the radiation image capture system 10 of the present exemplary embodiment.

Figure 3:
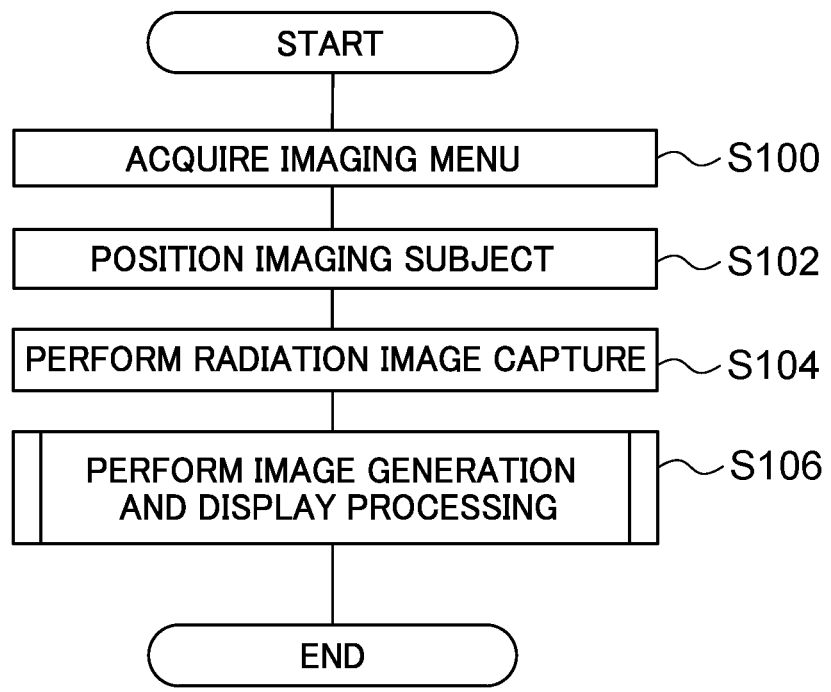
FIG. 3 is a flowchart illustrating a flow of a radiation image capture operation by a radiation image capture system of the present exemplary embodiment.

First, explanation follows regarding the overall flow of radiation image capture by the radiation image capture system 10 of the present exemplary embodiment. FIG. 3 is a flowchart illustrating the overall flow of radiation image capture by the radiation image capture system 10 of the present exemplary embodiment.

At step S100 in FIG. 3, the overall controller 50 of the console 20 acquires an imaging menu. The imaging menu includes imaging conditions such as the tube voltage of the radiation source 42, the dose of radiation R to be radiated onto the imaging subject W (mAs value), as well as information relating to the imaging subject W. The overall controller 50 may acquire an imaging menu from an external system through the I/F 62, for example, or may acquire an imaging menu input to the operation section 60 by the operator.

Next, at step S102, the operator positions the imaging subject W.

Next, at step S104, the overall controller 50 of the console 20 emits radiation R from the radiation radiating device 16 according to the acquired imaging menu, and the radiation R that has passed through the imaging subject W is detected by the radiation detectors 14, such that a radiation image is captured by the radiation image capture device 12.

Figure 4:
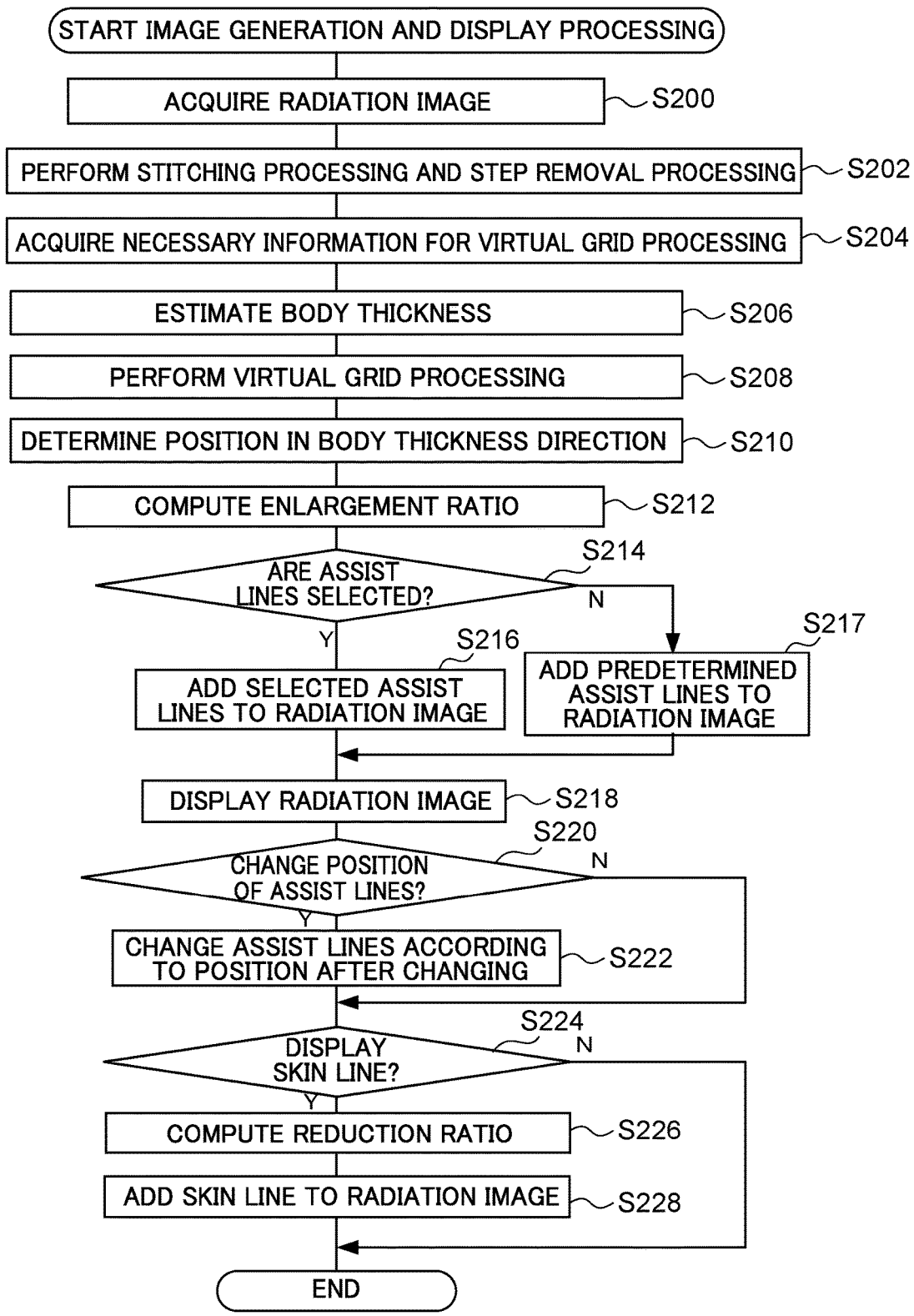
FIG. 4 is a flowchart illustrating a flow of image generation and display processing executed by a console of the present exemplary embodiment.

Next, at step S106, the overall controller 50 of the console 20 executes the image generation and display processing illustrated in FIG. 4.

At step S200, the overall controller 50 acquires the radiation image. Specifically, the overall controller 50 acquires each of the radiation images captured by each radiation detector 14 of the radiation detector group 15 from the storage section 52.

Next, at step S202, the overall controller 50 performs the stitching processing and step removal processing previously described. A long-length radiation image using the whole of the radiation image capture device 12 is obtained by performing this processing.

Next, at step S204, the overall controller 50 acquires the necessary information to perform virtual grid processing. The information needed to perform virtual grid processing should be information according to the type of virtual grid virtually applied to remove scattered radiation, the method of virtual grid processing, described later, and so on. Thus, the overall controller 50 of the present exemplary embodiment first identifies the type of virtual grid, and acquires the necessary information for virtual grid processing according to the identified type of virtual grid, the method of virtual grid processing, described later, and so on.

Note that there is no particular limitation to the method of identifying the type of virtual grid, and, for example, the type of virtual grid may be acquired from the imaging menu acquired at step S100 in cases in which the type of virtual grid is included in the imaging menu. The amount of scattered radiation R differs according to the body thickness of the imaging subject W, such that the greater the body thickness of the imaging subject W the greater the amount of scattered radiation, and the distribution of the scattered radiation differs according to the imaging site of the imaging subject W. The body thickness of the imaging subject W is related to the body type and build (such as the height and weight), the age, the gender, and so on of the imaging subject W. Information expressing a correspondence relationship between pre-selected information from out of the above information and the type of virtual grid is thereby stored in the storage section 52 as information relating to the imaging subject W. The type of virtual grid corresponding to the information relating to the imaging subject W contained in the imaging menu acquired at step S100 may be identified based on the information expressing the correspondence relationship stored in the storage section 52.

There is no particular limitation to the information necessary to perform virtual grid processing, and it includes, for example, scattered radiation transmissivity Ts in cases in which a virtual grid is applied, and transmissivity Tp of primary radiation that passes through the imaging subject W and is radiated directly onto the radiation detectors 14 (primary radiation transmissivity Tp). Note that the scattered radiation transmissivity Ts and the primary radiation transmissivity Tp are each values between 0 and 1.

Next, at step S206, the overall controller 50 estimates the body thickness of the imaging subject W. There is no particular limitation to the method of estimating the body thickness.

For example, the method described in JP-A No. 2015-192846 may be employed to estimate the body thickness. Alternatively, for example, when (x, y) are coordinates of pixel positions in the radiation image, and assuming the distribution of brightness in the radiation image to substantially match the distribution of body thickness of the imaging subject W, the body thickness distribution T (x, y) may be computed by converting pixel values in the radiation image to thickness using a linear attenuation coefficient value. Alternatively, for example, an estimate image from combining an estimated primary radiation image obtained when radiation R is radiated onto a virtual model M and captured and an estimate scattered radiation image may be generated to correct the body thickness distribution of the virtual model M. By reducing the difference between the estimate image and the radiation image of the imaging subject W, the body thickness distribution is corrected and the estimate image is made to more closely resemble the radiation image of the imaging subject W, based on the difference between the estimate image and the radiation image of the imaging subject W. This corrected body thickness distribution of the virtual model M may be determined to be the body thickness distribution of the imaging subject W.

The body thickness of the imaging subject W is related to the body type and build, the age, the gender, and so on of the imaging subject W, as described above, and so the overall controller 50 may, for example, estimate the body thickness based on this information. Sensors or the like used to measure the body thickness of the imaging subject W may be installed to the radiation image capture device 12 in advance, for example, and the body thickness of the imaging subject W measured using these body thickness measurement sensors.

Next, at step S208, the overall controller 50 executes the virtual grid processing previously described on the radiation image obtained through the above processing. The influence of scattered radiation included in the radiation image is thereby suppressed.

Next, at step S210, the overall controller 50 determines a position in the body thickness direction. Note that the position in the body thickness direction refers to a position inside the imaging subject W determined based on the body thickness. In the present exemplary embodiment, as described later, this is a position where a predetermined member for adding assist lines is conjectured to have been disposed.

Namely, hitherto, in a radiation image capturing a site of interest, such as an affected region in the imaging site of the imaging subject W or a site the doctor wants to observe, assist lines have sometimes been added to the radiation image in order to assist observation of the site of interest. As technology to add assist lines, for example, technology is known in which a lattice patterned plate for adding assist lines is provided as a predetermined member between the imaging subject W and the radiation image capture device 12, and the lattice formed by the plate for adding assist lines is imprinted as a ghost image onto the radiation image.

Figure 5:
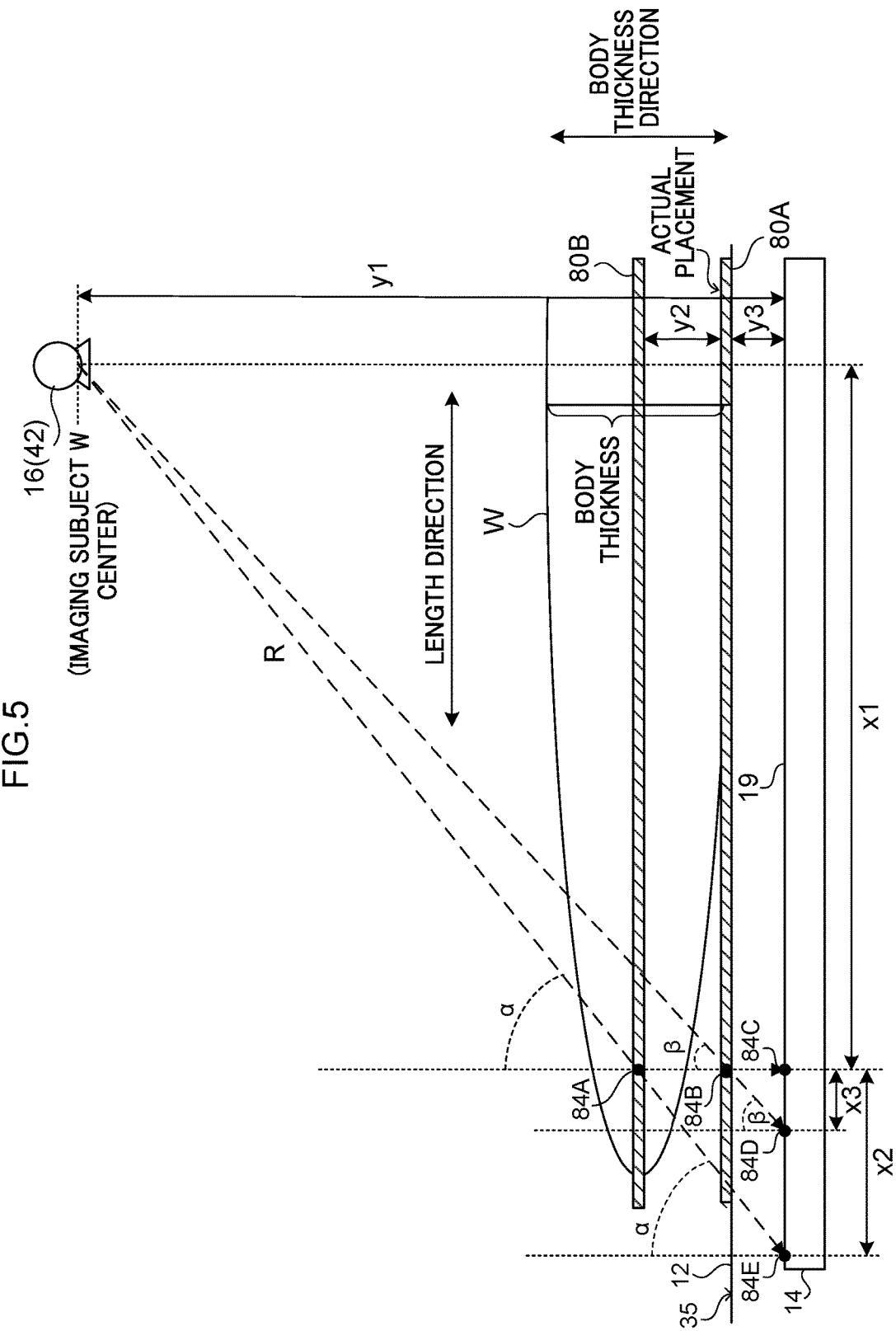
FIG. 5 is a schematic view explaining a position where radiation that has passed through an imaging subject is radiated onto a detection face of a radiation detector of a radiation image capture device.

When a predetermined member is actually employed as described above, the predetermined member is provided between the imaging subject W and the radiation image capture device 12. However, it is sometimes difficult to display the assist lines in a suitable position on the radiation image when the predetermined member is disposed in this manner. Explanation follows regarding such a case, with reference to FIG. 5. FIG. 5 is a schematic diagram for explaining a position where radiation R that has passed through the imaging subject W is radiated onto the detection face 19 of a radiation detector 14 of the radiation image capture device 12. Note that for ease of illustration in FIG. 5, the radiation source 42 is provided in a position facing a central portion of an imaging face 35 of the radiation image capture device 12, and the imaging subject is illustrated from an end portion to a central portion in the length direction of the radiation image capture device 12. For ease of explanation, there is only one radiation detector 14 (detection face 19). A position where a site of interest 84A of the imaging subject W is imprinted onto the radiation image (a position where the radiation R arrives at the detection face 19) is explained as a specific example.

In cases in which a predetermined member 80A has been disposed between the imaging subject W and the radiation image capture device 12 as illustrated in FIG. 5, radiation R that has passed through the site of interest 84A arrives on the detection face 19 at an arrival point 84E that is offset from a location 84C of the detection face 19 positioned directly below the site of interest 84A, according to the obliqueness of the incident radiation R. A site 84B on the predetermined member 80A positioned directly below the site of interest 84A of the imaging subject W arrives at an arrival point 84D that is offset from the location 84C of the detection face 19, according to the obliqueness of the incident radiation R. Namely, the radiation image of the site of interest 84A is imprinted at the position of the arrival point 84E, and the radiation image of the site 84B is imprinted at the position of the arrival point 84D.

As illustrated in FIG. 5, the arrival point 84D and the arrival point 84E are in different positions. Thus, in cases in which the doctor wants to add assist lines in order to observe the site of interest 84A, the doctor needs to dispose the site 84B of the predetermined member 80A in a position that is offset from directly below the site of interest 84A in the direction of the end portion. The distance between the arrival point 84D and the arrival point 84E (x2−x3) changes depending on the angles of incidence α and β of the radiation R onto the site of interest 84A and the site 84B. The larger the difference between the angle of incidence α and the angle of incidence β, the further this distance becomes. In cases in which there are plural sites of interest 84A, there is a higher possibility that the assist lines cannot be added in suitable positions with respect to all the sites of interest 84A.

In contrast thereto, the console 20 of the present exemplary embodiment enables assist lines to be displayed in a suitable position on a radiation image without actually employing a predetermined member such as a plate for adding assist lines. Namely, in order to reduce the above-described distance (x2−x3) between the arrival point 84D and the arrival point 84E, the site 84B of the predetermined member 80A should be in a position close to the site of interest 84A. A predetermined member 80B is preferably provided so as to make the site 84B of the predetermined member 80A closer to the site of interest 84A. However, as illustrated in FIG. 5, in such cases the position where the predetermined member 80B would be provided would be inside the body of the imaging subject W. Thus, in the console 20 of the present exemplary embodiment, assist lines that would have been expected to be obtained due to the predetermined member 80B are generated by the overall controller 50 and added to the radiation image. Thus, first, at step S210, the position of the site of interest 84A (the position of the predetermined member 80B) in the body thickness direction of the imaging subject W is determined in the following manner.

Namely, in cases in which an image is captured by a comparatively large, and particularly long-length radiation image capture device 12 as in the radiation image capture device 12 of the present exemplary embodiment, there is often a desire to observe the state of a bone or the condition of the skeleton, and so an example is given in which a leg bone or spine is the site of interest 84A. In cases in which the imaging subject W is a human body, the position of a leg bone or spine, etc. of the imaging subject W can be approximated to the vicinity of the center in the body thickness direction. Thus, the console 20 of the present exemplary embodiment determines a position at half the body thickness estimated at step S206, more specifically, a position separated from the imaging face 35 (a face at the side of the casing 13 facing the radiation radiating device 16) of the radiation image capture device 12 by a distance of ½ (50%) of the body thickness in the body thickness direction is determined as the position in the body thickness direction.

Although the position of a leg bone or spine, etc. of the imaging subject W is approximated to the vicinity of the center in the body thickness direction as described above, the position is not always in the vicinity of the center, depending on the build of the imaging subject W and so on. Moreover, the position of a bone (the site of interest) is not in the vicinity of the center in the body thickness direction in the case of rib bones and so on, regardless of the build, etc. of the imaging subject W. In cases in which the site of interest is not a bone, the position of the site of interest is not always in the vicinity of the center in the body thickness direction. Even if the site of interest is a leg bone or spine, etc., the position thereof sometimes differs depending on the direction in which the imaging subject W is captured.

Specifically, the position of the site of interest sometimes differs when one side of the imaging subject W is captured compared to when their front or back is captured, and the site of interest is not always in the vicinity of the center. Thus, configuration may be such that the position in the body thickness direction is predetermined according to at least one out of the imaging site or the imaging direction, and a correspondence relationship is pre-stored in the storage section 52 between the at least one out of the imaging site or the imaging direction and the position in the body thickness direction. The overall controller 50 then acquires the imaging site or the imaging direction from the imaging menu or the like, and determines the body thickness corresponding to the imaging site or imaging direction based on the correspondence relationship stored in the storage section 52.

Next, at step S212, the overall controller 50 computes an enlargement ratio K of the above-described assist lines. In cases in which there is a desire to add assist lines so as to be aligned with the radiation image of the site of interest 84A in the example illustrated in FIG. 5, the assist lines should be added at a position corresponding to the arrival point 84E. Thus, in the present exemplary embodiment, the assist lines are added at a position on the radiation image of the site of interest 84A, this being the position at the arrival point 84E, rather than the position of the assist lines being a position directly below the site of interest 84A (the location 84C). Specifically, in the case illustrated in FIG. 5, the position of the assist lines is set at a distance of the distance x2 added to a distance x1 (x1+x2), wherein the distance x1 is a distance in the length direction from the radiation source 42. Thus, the enlargement ratio K can be obtained using Equation (1) below.

$$\text{Enlargement ratio } K=(x1+x2)/x1 \qquad (1)$$

In the case illustrated in FIG. 5, the relationship of Equation (2) below is satisfied.

$$\tan \alpha = x1/(y1-(y2+y3)) = (x1+x2)/y1 = x2/(y2+y3) \qquad (2)$$

In Equation (2), y1 is a distance from the detection face 19 of the radiation detector 14 to the radiation source 42 (what is referred to as source to image receptor distance: SID). The distance y1 is a distance determined according to the positions of the radiation source 42 and the radiation detector 14. There is no particular limitation to the method by which the overall controller 50 acquires the distance y1, which may be acquired from the imaging menu, for example, if included as an imaging condition in the imaging menu. The distance y1 may alternatively be acquired based on information indicating the position of the radiation source 42 input to the operation section 60 or the like by the operator, for example.

In Equation (2), y2 is a distance in the body thickness direction from the imaging face 35 of the radiation image capture device 12 to the site of interest 84A. The distance y2 is equivalent to the position in the body thickness direction determined at step S210.

In Equation (2), y3 is a distance in the body thickness direction from the detection face 19 of the radiation detector 14 to the imaging face 35. The distance y3 is a distance that is determined according to the design of the radiation image capture device 12. There is no particular limitation to the method by which the overall controller 50 obtains the distance y3, which may be stored in the individual storage section 32 of the respective radiation image capture device 12, for example, such that the console 20 acquires the distance y3 stored in the storage section 32 through the I/F 62, 34. The distance y3 may be stored in a location other than the storage section 32, such as the storage section 52 of the console 20 or a device other than the radiation image capture system 10; however, the distance y3 sometimes differs depending on the type, size, etc. of the radiation image capture device 12. Thus, in such cases, a mode may be applied in which information indicating the type and size of the radiation image capture device 12, and the distance y3, are stored associated with each other, and the overall controller 50 acquires the distance y3 corresponding to the type and size of the radiation image capture device 12 used for imaging.

Note that, although not illustrated in FIG. 5, the distance y3 differs for each radiation detector 14, and there are three distances y3 present in the radiation image capture device 12 of the present exemplary embodiment. Thus, a range of the distance x1 to be applied is predetermined for each of the three distances y3. The range of the distance x1 may be determined according to the positions of the respective radiation images captured by each radiation detector 14 in the radiation image captured using the whole of the radiation image capture device 12.

Based on Equation (2), the relationship in Equation (3) below is satisfied.

$$x2=x1(y2+y3)/(y1-y2-y3) \qquad (3)$$

In the present exemplary embodiment, the distance x1 is a known value. Thus, the enlargement ratio K can be obtained by applying Equation (3) to Equation (1).

Note that the enlargement ratio K in the length direction of the radiation image capture device 12 has been explained above with reference to FIG. 5; however, it goes without saying that the enlargement ratio K may also be obtained by Equation (1) in a direction intersecting the length direction of the radiation image capture device 12.

Next, at step S214, the overall controller 50 determines whether or not the type of assist lines has been selected. In the console 20 of the present exemplary embodiment, assist lines selected by the doctor from plural types of assist line can be added to the radiation image.

Figure 6A:
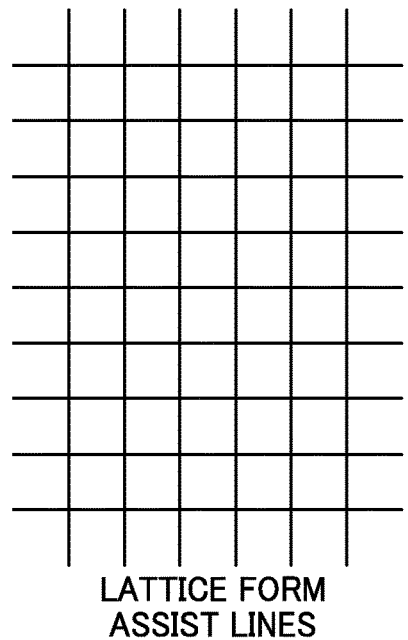
FIG. 6A is a schematic view illustrating an example of lattice form assist lines.
Figure 6B:
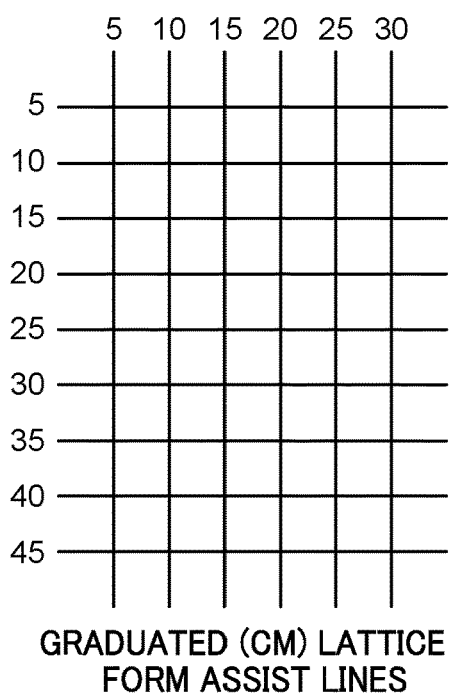
FIG. 6B is a schematic view illustrating an example of lattice form assist lines with units of graduation in cm.
Figure 6C:
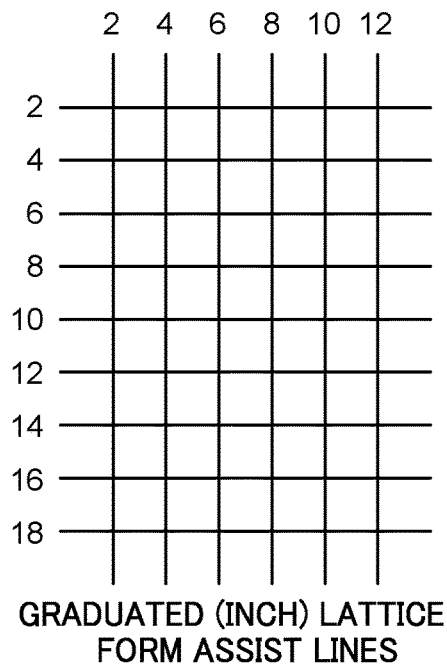
FIG. 6C is a schematic view illustrating an example of lattice form assist lines with units of graduation in inches.
Figure 6D:
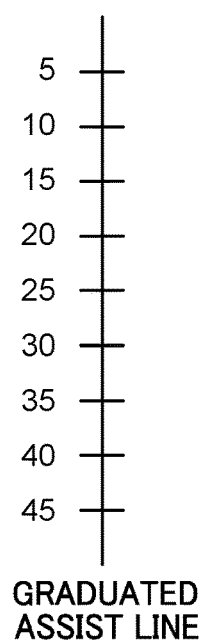
FIG. 6D is a schematic view illustrating an example of a graduated assist line.
Figure 6E:
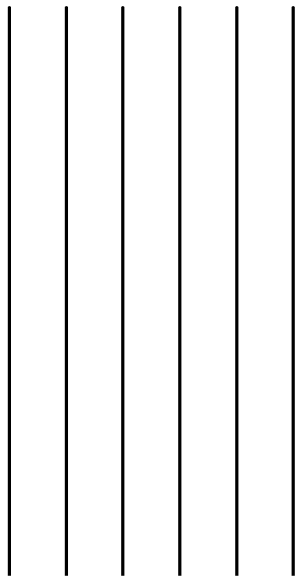
FIG. 6E is a schematic view illustrating an example of straight-line form assist lines.

The assist lines illustrated in FIGS. 6A to 6E are examples of types of assist line that can be added by the console 20 of the present exemplary embodiment. FIG. 6A illustrates an example in which lattice form assist lines are formed by plural straight lines that intersect each other (that are orthogonal to each other in the present exemplary embodiment) (hereafter referred to as "lattice form assist lines"). FIG. 6B illustrates an example of graduated lattice form assist lines with units of graduation in centimeters has been appended to the lattice form assist lines illustrated in FIG. 6A. FIG. 6C illustrates an example of graduated lattice form assist lines with units of graduation in inches has been appended to the lattice form assist lines illustrated in FIG. 6A. FIG. 6D illustrates an example of a graduated assist line in which a graduation has been appended to a display illustrating a scale (hereafter referred to as a "graduated assist line"). FIG. 6E illustrates an example of straight-line form assist lines in which straight lines are disposed every specific spacing (hereafter referred to as "straight-line form assist lines"). The types of assist line are not limited to those illustrated in FIGS. 6A to 6E. For example, types of assist line that may be employed include the graduated assist line illustrated in FIG. 6D from which the numbers expressing graduation have omitted, or the straight-line form assist lines illustrated in FIG. 6E to which values have been added corresponding to a specific spacing. The shape, size, etc. of the assist lines are also not limited to those illustrated in FIGS. 6A to 6E.

The doctor can select the type of assist lines to be added to the radiation image, and instruct the console 20 of the selected type of assist lines. There is no particular limitation to the method by which the doctor instructs the type of assist lines, and the doctor may input information indicating the type of assist lines they want to add to the radiation image using, for example, the operation section 60. When this is performed, the overall controller 50 preferably displays sample images of the respective assist lines, such as the images illustrated in FIGS. 6A to 6E, on the display section 56 as a reference for the doctor selecting the type of assist lines.

In the present exemplary embodiment, when information indicating the type of assist lines has been input using the operation section 60, affirmative determination is made at step S214, and processing transitions to step S216.

Figure 7:
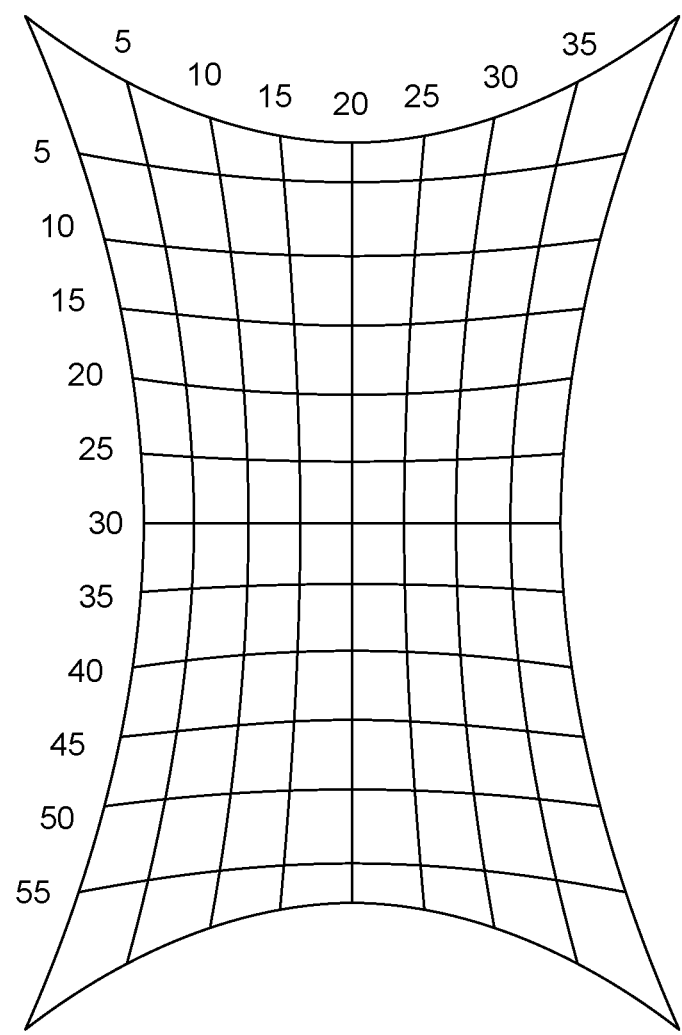
FIG. 7 is a schematic view illustrating an example of assist lines illustrated by plural lines disposed in a distorted spool shape.

At step S216, the overall controller 50 adds the selected assist lines to the radiation image, and processing transitions to step S218. Specifically, an assist line image, having each of the straight lines of the assist lines selected by the doctor enlarged using the enlargement ratio K obtained by the processing of step S212, is superimposed on the radiation image after the virtual grid processing of step S208 has been performed. For example, in cases in which the graduated lattice form assist lines illustrated in FIG. 6B have been selected as the assist lines, the assist lines enlarged by applying the enlargement ratio K become the assist lines illustrated by plural lines disposed in a distorted spool shape, as illustrated as an example in FIG. 7. Note that there is no change to the values applied for graduation in such cases.

At step S214, negative determination is made in cases in which information indicating the type of assist lines has not been input using the operation section 60 after a specific duration has elapsed, and processing transitions to step S217.

At step S217, the overall controller 50 adds predetermined assist lines to the radiation image, after which processing transitions to step S218. There is no particular limitation to the predetermined assist lines, which may be predetermined by the console 20.

Figure 8:
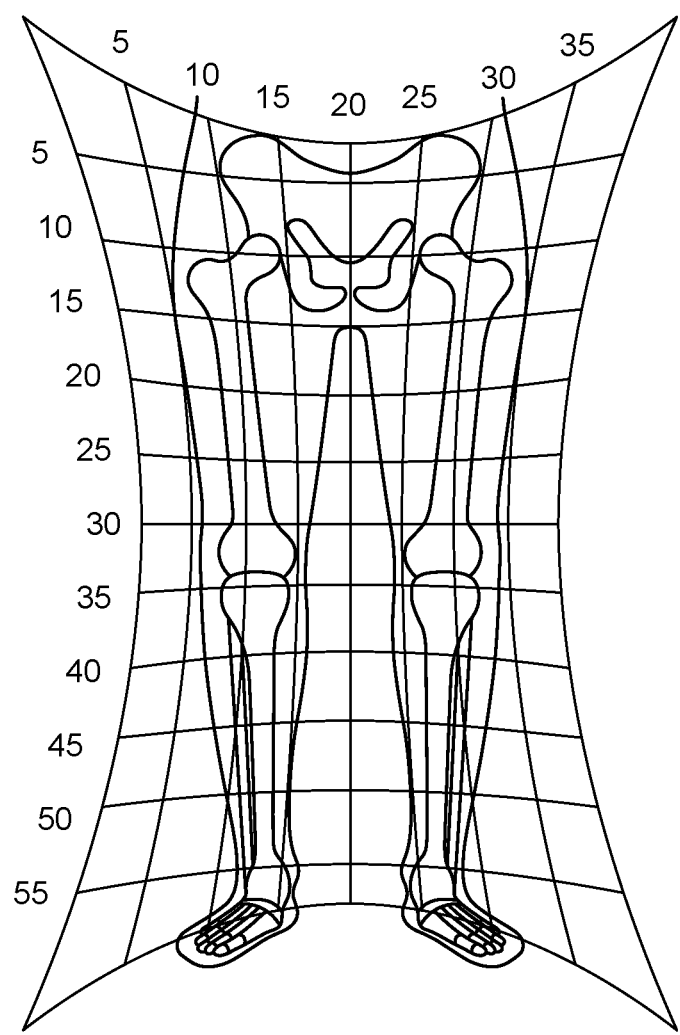
FIG. 8 is a schematic view illustrating an example of a radiation image to which assist lines have been added.

At step S218, the overall controller 50 displays the radiation image (the radiation image after virtual grid processing) with the added assist lines on the display section 56. An example is illustrated in FIG. 8 of a case in which the assist lines illustrated in FIG. 7 have been added to a radiation image for an imaging site of the legs. Note that in the present exemplary embodiment, visibility on the display section 56 of the assist lines displayed on a black and white radiation image is facilitated by using pairs of a black and a white line, namely two lines, to represent each of the straight lines. Note that there is no particular limitation to the color of the assist lines, which may be another color such as red, and may be changed according to an instruction by the doctor.

Next, at step S220, the overall controller 50 determines whether or not to change the position of the assist lines. In the console 20 of the present exemplary embodiment, the position of the assist lines added to the radiation image can be changed by the doctor. In the console 20 of the present exemplary embodiment, the position of the assist line image on the radiation image (hereafter simply referred to as "assist line position") may be changed in either a direction parallel to the imaging face 35 of the radiation image capture device 12, or the body thickness direction of the imaging subject W. In the console 20 of the present exemplary embodiment, in order to change the assist line position the doctor uses the operation section 60 to instruct the position of the assist lines after changing.

Figure 9:
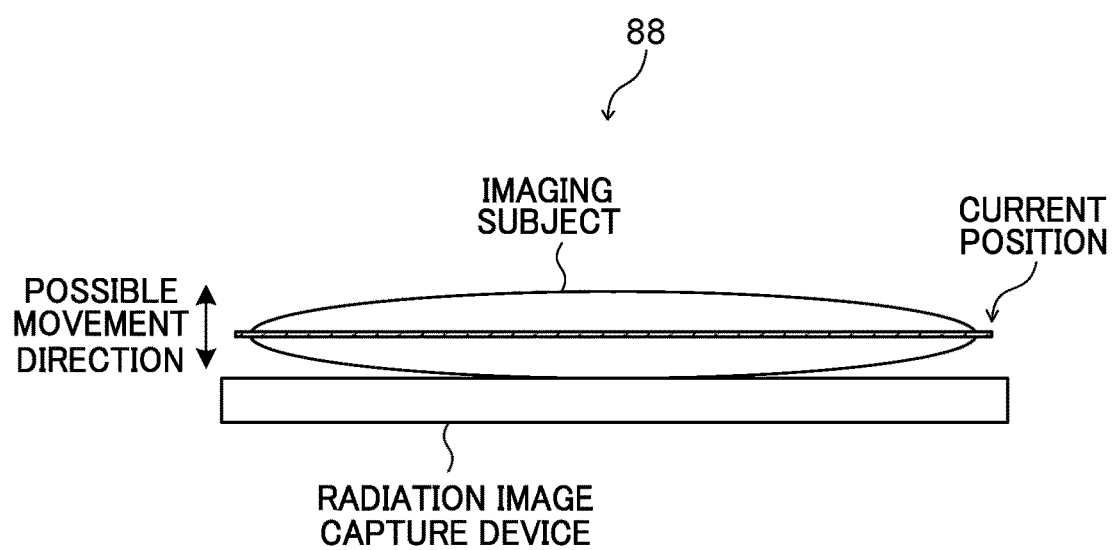
FIG. 9 is a schematic view illustrating an example of an image used to change assist line position.

Note that, in cases in which the doctor wants to change the assist line position in the body thickness direction of the imaging subject W, the overall controller 50 preferably displays an image to assist the doctor in changing the assist line position on the display section 56. For example, in cases in which an instruction to change the assist line position in the body thickness direction of the imaging subject W has been received through the operation section 60 from the doctor, the overall controller 50 preferably displays an image used to change assist line position 88 on the display section 56, as illustrated by the example in FIG. 9. The image used to change assist line position 88 illustrated in the example in FIG. 9 includes an image illustrating the radiation image capture device 12, the imaging subject W, and the current position of the assist lines in the body thickness direction of the imaging subject W. The image used to change assist line position 88 also includes information indicating possible directions to move the assist line position (the body thickness direction of the imaging subject W in this case). In cases in which the doctor wants to move the assist lines in the body thickness direction of the imaging subject W, for example, an instruction regarding the position of the assist lines after changing may be performed by moving (what is referred to as dragging and dropping) the image illustrating the current position of the assist lines in the image used to change assist line position 88 to the desired changed position using an operation section 60 such as a mouse.

In cases in which the doctor wants to change the assist line position in a direction parallel to the imaging face 35, for example, an instruction regarding the assist line position after changing may be performed by moving (what is referred to as dragging and dropping) the assist line image added to the radiation image displayed on the display section 56 as illustrated in the example in FIG. 8 to the desired changed position using the operation section 60 such as a mouse.

At step S220, affirmative determination is made in cases in which an instruction regarding an assist line position after changing has been received from the doctor through the operation section 60, and processing transitions to step S222.

At step S222, the overall controller 50 changes the assist line image added to the radiation image displayed on the display section 56 to the image of the assist lines corresponding to the assist line position after changing, after which processing transitions to step S224. Specifically, the overall controller 50 derives the movement amount of the assist lines by deducting the assist line position prior to changing from the received assist line position after changing, and changes the position of each straight line contained in the assist lines according to the derived movement amount. The overall controller 50 then changes the assist lines by enlarging each straight line contained in the assist lines using the enlargement ratio K according to the position after changing, and displays this assist line image on the display section 56 instead of the assist line image currently displayed.

Negative determination is made in cases in which an instruction regarding the assist line position after changing has not been received through the operation section 60 after a specific duration has elapsed at step S220, and processing transitions to step S224.

At step S224, the overall controller 50 determines whether or not to display the skin line of the imaging subject W. In the present exemplary embodiment, the skin line refers to an outline of the imaging subject W. As previously described with reference to FIG. 5, the position of the site of interest 84A becomes the position of the arrival point 84E in the radiation image, and so the image of the imaging subject W is enlarged according to the obliqueness of the incident radiation R. The nearer to the vicinity of an end portion of the radiation image capture device 12, the larger the angle of incidence, such that the enlargement ratio K of the image of the imaging subject W is increased, and, in geometric terms, the image of the imaging subject W is caused to bulge out greatly compared to the actual imaging subject W. In the console 20 of the present exemplary embodiment, information indicating the actual size of the imaging subject W can be displayed in the radiation image. In the console 20 of the present exemplary embodiment, an image (line image) illustrating the original skin line of the imaging subject W can be displayed in the radiation image as information indicating the size of the imaging subject W. In cases in which the doctor wants the skin line to be displayed, the doctor uses the operation section 60 to perform display instruction so as to display the skin line.

At step S224, negative determination is made in cases in which the display instruction has not been input after a specific duration has elapsed, and the present image generation and display processing is ended. Affirmative determination is made in cases in which a display instruction has been input at step S224, and processing transitions to step S226.

At step S226, the overall controller 50 computes a reduction ratio S of the skin line of the imaging subject W. The reduction ratio S can be obtained from Equation (4) below, derived using Equation (1).

$$\text{Reduction ratio } S = x1/(x1+x2) \qquad (4)$$

Figure 10:
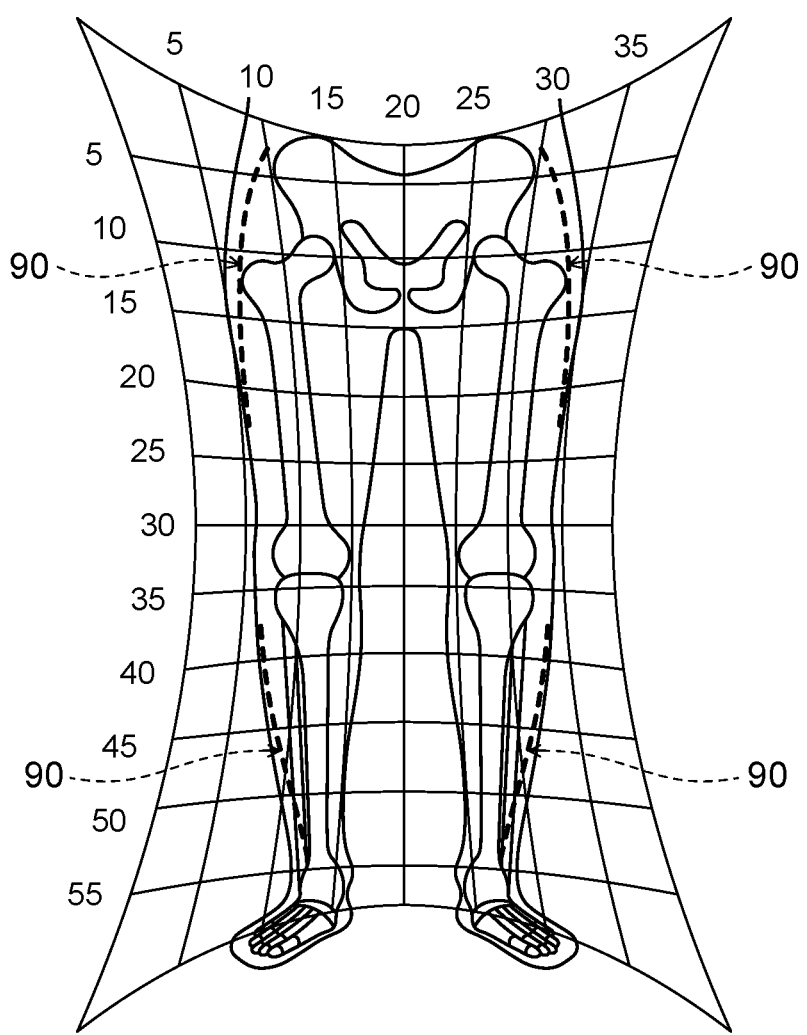
FIG. 10 is a schematic view illustrating an example of a radiation image to which assist lines and skin lines have been added.

Next, at step S228, as illustrated in the example in FIG. 10, the overall controller 50 adds images 90 illustrating the original skin line of the imaging subject W to the radiation image displayed on the display section 56, after which the present image generation and display processing is ended. Note that, of the original skin line of the imaging subject W, images illustrating the skin line on the inner thigh side of the imaging subject W are not displayed in the example illustrated in FIG. 10; however, images illustrating the skin line on the inner thigh side may also be displayed.

Specifically, the overall controller 50 first detects the skin line of the imaging subject W in the radiation image. Note that the radiation image referred to is the radiation image displayed on the display section 56, which is the radiation image after virtual grid processing, and the detected skin line bulges out further than the original skin line of the imaging subject W. The overall controller 50 then reduces the image illustrating the detected skin line using the reduction ratio S obtained at step S226, and adds the reduced image to the radiation image displayed on the display section 56. Note that when generating an assist line image as previously described, the distance y2 is set at ½ the body thickness (body thickness×0.5) due to the assumption that the imaging subject W is bone; however, for the skin line, the skin line is assumed to be most greatly bulged, more than for the imaging subject W of bones, at the front face side (the face side), and, so in the present exemplary embodiment, the distance y2 is set at 7/10 of the body thickness (body thickness×0.7) to generate an image illustrating the skin line.

After completing the image generation and display processing in this manner, the overall operation of radiation image capture is also ended.

As explained above, in the radiation image capture system 10 of the present exemplary embodiment, the overall controller 50 of the console 20 acquires a radiation image of the imaging subject W captured by the radiation image capture device 12 for radiographic imaging. The overall controller 50 also acquires body thickness information indicating the body thickness of the imaging subject W in the direction through which the radiation R passes. The overall controller 50 also adds to the radiation image an assist line image that would be expected to be obtained if a predetermined member had been disposed and captured at a position inside the imaging subject W determined based on the acquired body thickness information, or at a position between the imaging subject W and the radiation image capture device 12.

Thus, in the radiation image capture system 10 of the present exemplary embodiment, due to the overall controller 50 of the console 20 adding assist lines to the radiation image, there is no need to install an actual plate for adding assist lines. Thus, the console 20 of the present exemplary embodiment enables the work procedure of the operator to be improved, and reduces the need for an additional operator.

In the radiation image capture system 10 of the present exemplary embodiment, the overall controller 50 performs stitching processing and step removal processing because the radiation image capture device 12 includes plural radiation detectors 14. If an actual plate for adding assist lines were employed to add assist lines, there would be a concern that artifacts might be generated during the image-processing to the imprinted image of the plate for adding assist lines. For example, if a plate used to add lattice form assist lines were employed in order to add lattice form assist lines, there would be a high possibility of artifacts being generated in the latticed part thereof. In contrast thereto, there is no actual plate for adding assist lines in the console 20 of the present exemplary embodiment, and so there is no concern of such artifacts being generated.

Thus, the console 20 of the radiation image capture system 10 of the present exemplary embodiment enables assist lines to be added in consideration of the position of a site of interest in the body thickness direction, thereby enabling assist lines for assisting observation to be displayed at a suitable position in the radiation image.

Thus, the console 20 of the present exemplary embodiment enables reading and diagnosis by a doctor to be facilitated.

The radiation image capture system 10 of the present exemplary embodiment enables assist lines to be added without using an actual plate to add assist lines, thereby enabling the cost for a plate to add assist lines to be saved.

Note that in the present exemplary embodiment, a case has been explained in which the radiation image capture device 12 is employed for long-length imaging and includes plural radiation detectors 14; however, the radiation image capture device 12 may be used to capture the head or the chest, for example, rather than for long-length imaging, and may be configured including only one radiation detector 14. For ease of explanation below, cases in which the radiation image capture device 12 is used for long-length imaging as described above are referred to as "the above-described mode", and cases in which the radiation image capture device 12 is not employed for long-length imaging are referred to as "the present mode".

Figure 11:
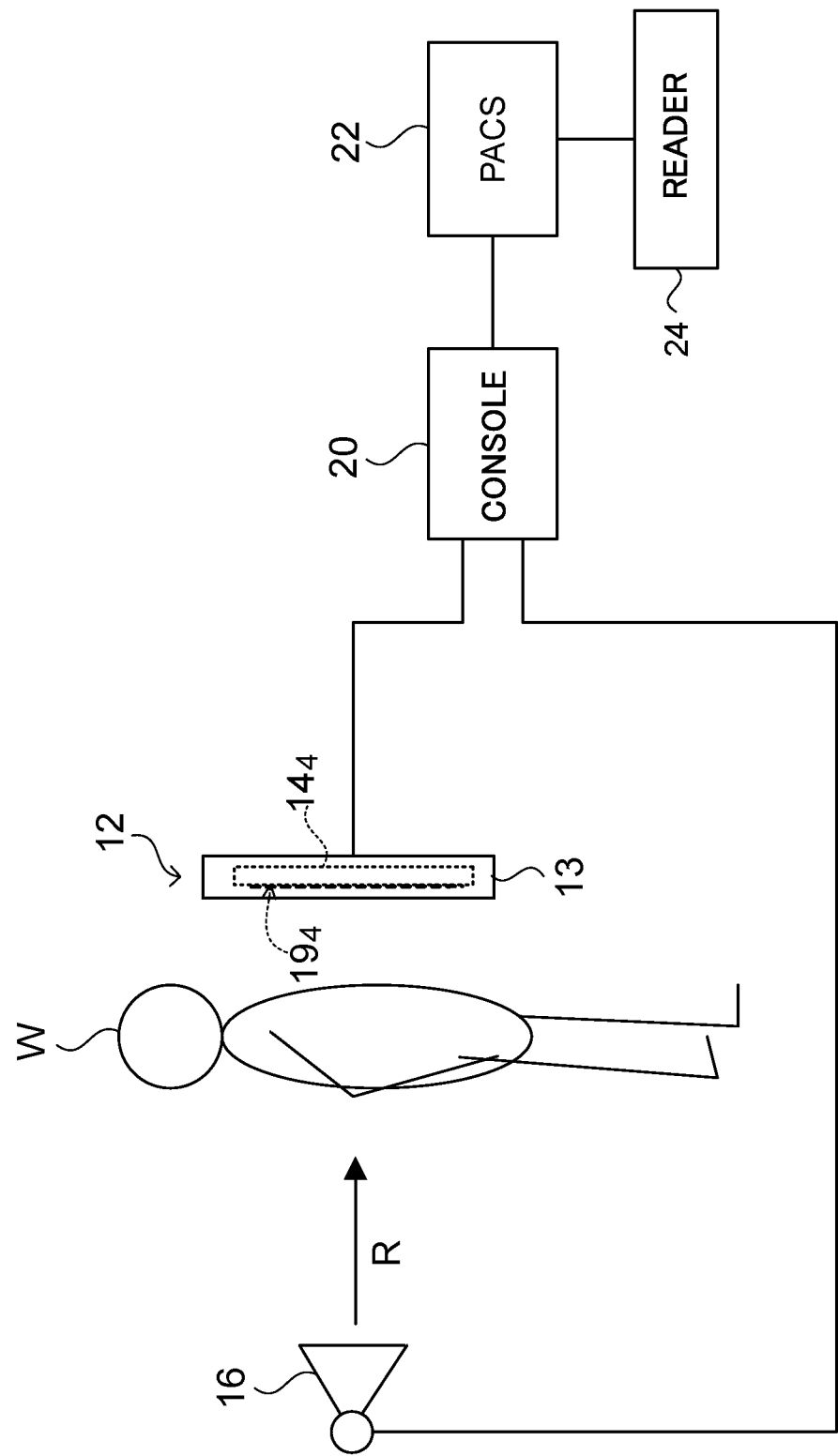
FIG. 11 is a configuration diagram illustrating a configuration of a radiation image capture system including a radiation image capture device that is not used for long-length imaging.
Figure 12:
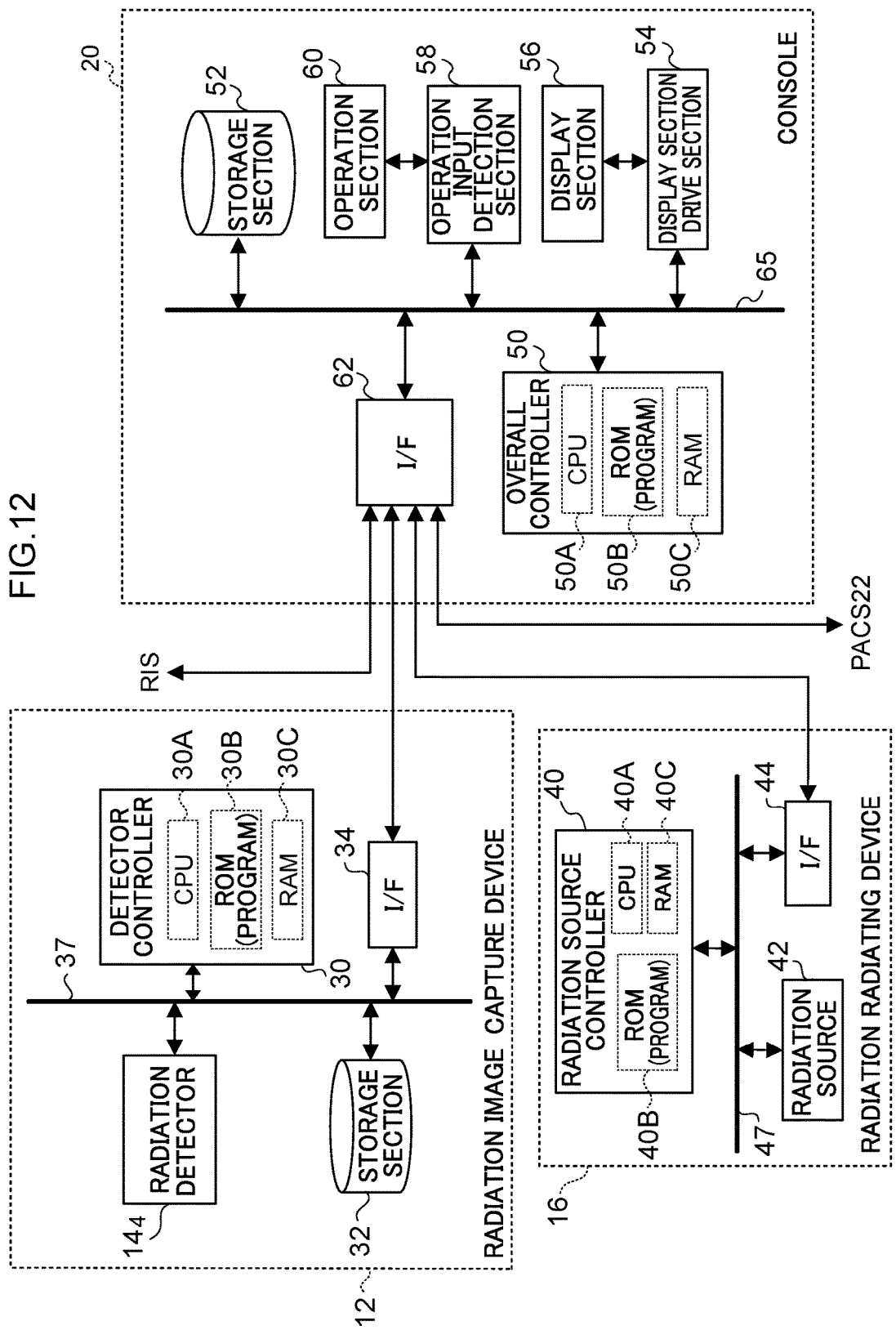
FIG. 12 is a block diagram illustrating a configuration of the radiation image capture system illustrated in FIG. 11.

FIGS. 11 and 12 illustrate a configuration of a radiation image capture system 10 of the present mode. A radiation image capture device 12 of the present mode illustrated in the example in FIGS. 11 and 12 is only equipped with a radiation detector $14_4$ including a detection face $19_4$, instead of the radiation detectors $14_1$ to $14_3$ included in the radiation image capture device 12 of the radiation image capture system 10 (see FIGS. 1 and 2) of the above-described mode. The radiation detector $14_4$ of the present mode has a similar configuration and size to each of the radiation detectors $14_1$ to $14_3$ of the above-described mode. Note that other configuration of the radiation image capture system 10 of the present mode is similar to that of the radiation image capture system 10 of the above-described mode.

An overall flow of radiation image capture by the radiation image capture system 10 of the present mode is similar to the overall flow of radiation image capture by the radiation image capture system 10 of the above-described mode (see FIG. 3); however, part of the image generation and display processing at step S106 thereof is different. In the radiation image capture device 12 of the present mode, only the radiation detector $14_4$ performs radiation image capture, and so the overall controller 50 does not need to perform the stitching processing or the step removal processing during the image-processing, in contrast to the image-processing performed by the overall controller 50 of the above-described mode. Thus, as illustrated in FIG. 13, in the image generation and display processing executed by the overall controller 50 of the console 20 of the present mode, the fact that the processing of step S202 is not performed differs from the image generation and display processing executed by the overall controller 50 of the console 20 of the above-described mode (see FIG. 3). Each of the other steps of the image generation and display processing is similar in the present mode and the above-described mode.

Thus, in the present mode also, the overall controller 50 of the console 20 acquires body thickness information indicating the body thickness of the imaging subject W in the direction through which the radiation R passes, and adds to the radiation image an assist line image that would be expected to be obtained if a predetermined member had been disposed and captured at a position inside the imaging subject W determined based on the acquired body thickness information, or at a position between the imaging subject W and the radiation image capture device 12.

Even in cases in which the radiation image capture device 12 only includes the radiation detector $14_4$ as in the present mode, the radiation R is obliquely incident to locations that are not directly below the radiation source 42, such as an end portion of the detection face $19_4$ of the radiation detector $14_4$, such that the image of the imaging subject W is enlarged. However, the console 20 of the present mode enables assist lines for assisting observation of a site of interest to be displayed in a suitable position on the radiation image, similarly to the above-described mode.

Namely, in cases in which radiation R is obliquely incident to the detection faces 19 of the radiation detectors 14, the image of the imaging subject W is enlarged according to the angle of incidence, regardless of the number of radiation detectors 14 or the size of the radiation detectors 14 (detection faces 19) included in the radiation image capture device 12; however, applying the present embodiment enables assist lines for assisting observation of a site of interest to be displayed in a suitable position on the radiation image.

Note that the further away the incident position is on the radiation detector 14 of radiation R that has passed through the imaging subject W from a position directly below the radiation source 42, the more obliquely the incidence of the radiation R to the radiation detector 14. Thus, the further away the incident position is of radiation Ron the radiation detector 14 from a position directly below the radiation source 42, and the more the image of the imaging subject W is enlarged. In particular, in cases, as in the above-described mode, in which the imaging site of the imaging subject W is comparatively large, such as when capturing the entire lower leg, enlargement of the image of the imaging subject W becomes more obvious due to the position where radiation R is incident to the radiation detector 14 being further away from a position directly below the radiation source 42, and there is a higher possibility of the assist lines not being displayed in a suitable position. Even greater advantageous effects can therefore be obtained when the present embodiment is applied to a radiation image capture device 12 used for long-length imaging, as previously described.

In the image generation and display processing executed by the console 20 of the present exemplary embodiment, the original skin line of the imaging subject W is added to the radiation image and displayed on the display section 56; however, the method of displaying the original size of the imaging subject W is not limited thereto. For example, the radiation image itself, or the entire image of the imaging subject Win the radiation image, may be reduced by the reduction ratio S, and un-enlarged assist lines may be added as they are to the reduced radiation image.

In the image generation and display processing executed by the console 20 of the present exemplary embodiment, predetermined assist lines are added to the radiation image in cases in which assist lines have not been selected at step S214; however, the radiation image may be displayed alone without adding any assist lines in such cases. Note that configuration may be made such that the doctor can change whether or not to add assist lines (whether to display assist lines) to the radiation image.

The manner of computing the enlargement ratio K is not limited to that of the present exemplary embodiment. For example, a sign such as a marker may be captured together with the imaging subject W, and the enlargement ratio K computed based on the size of the image of the sign in the radiation image.

Note that in the radiation image capture system 10 of the present exemplary embodiment, a case has been explained in which the overall controller 50 of the console 20 functions as each section of an image-processing device; however, there is no limitation to the present exemplary embodiment, and, for example, another device such as the reader 24 may include some or all of the functions of the sections of an image-processing device.

In the radiation detector group 15 of the present exemplary embodiment, the radiation detector $14_1$ is disposed nearest to the radiation radiating device 16, and the radiation detector $14_3$ is disposed furthest from the radiation radiating device 16; however, the placement of the radiation detectors 14 is not limited to that in the present exemplary embodiment. For example, the radiation detectors 14 may be disposed in what is referred to as a terraced shape in which the radiation detectors $14_1$, $14_3$ are disposed nearest to the radiation radiating device 16, and the radiation detector $14_2$ is disposed furthest from the radiation radiating device 16. Alternatively, for example, the radiation detectors 14 may be disposed in what is referred to as a terraced shape in which the radiation detectors $14_1$, $14_3$ are disposed furthest from the radiation radiating device 16, and the radiation detector $14_2$ is disposed nearest to the radiation radiating device 16. In the radiation detector group 15 of the present exemplary embodiment, the end portions of the respective radiation detectors 14 are overlapped with each other; however, the respective radiation detectors 14 may be disposed in a state in which the detection faces 19 of the respective radiation detectors 14 are arranged in the same plane without the end portions overlapping each other. The radiation detectors 14 may also be disposed in a matrix shape, such as 2 by 2 array.

In the present exemplary embodiment, a case has been explained in which plural radiation detectors 14 (the radiation detector group 15) are included inside one casing 13; however, there is no limitation thereto. For example, each radiation detector 14 may be provided inside its own individual casing.

In the present exemplary embodiment, a case has been explained in which the imaging subject W is a human body; however, the imaging subject W is not limited to being a human body, and may be a body other than a human, such as an animal or a plant.

There is no particular limitation to the type of radiation R of the present exemplary embodiment, and X-rays or γ rays, for example, may be applied.

Configurations of the radiation image capture system 10, the radiation detector group 15, the radiation detectors 14, the console 20, etc. explained in the present exemplary embodiment are merely examples thereof, and obviously modifications may be implemented depending on the circumstances within a range not departing from the spirit of the present invention.

The addition section of the image-processing device according to an aspect of the present invention may be configured to also add to the radiation image information indicating the size of the imaging subject at the position determined based on the body thickness information.

Moreover, in such cases, the information indicating the size of the imaging subject may be a skin line of the imaging subject.

The image-processing device according to an aspect of the present invention may further include a receiving section configured to receive information indicating a change to the position inside the imaging subject and information indicating the position inside the imaging subject after the change. In cases in which the receiving section has received information indicating a change, the addition section may be configured to change the assist line image added to the radiation image to an assist line image that would be expected to be obtained if the member had been disposed and captured at the position inside the imaging subject after the change.

The addition section of the image-processing device according to an aspect of the present invention may be configured to determine the position inside the imaging subject depending on an imaging site of the imaging subject.

The body thickness information of the image-processing device according to an aspect of the present invention may be information indicating a body thickness of the imaging subject estimated by acquiring imaging conditions of the radiation image, and be based on properties of a virtual grid that is a virtual grid virtually applied to remove scattered radiation during capturing of the radiation image in order to set a removal amount for scattered radiation, and based on the imaging conditions.

The body thickness information of the image-processing device according to an aspect of the present invention may be information indicating a body thickness of the imaging subject estimated based on information relating to at least one from out of the age, gender, or build of the imaging subject.

The addition section of the image-processing device according to an aspect of the present invention may be configured to add the assist line image to the radiation image corrected according to a position of a region of the imaging subject irradiated by the radiation, and a position of a radiation source that radiates the radiation.

The radiation image capture device in the image-processing device according to an aspect of the present invention may be a radiation image capture device used for long-length imaging.

The radiation image capture device in the image-processing device according to an aspect of the present invention may include plural radiation detectors that each include a detection face configured to detect radiation disposed with their detection faces in a state arranged to capture a radiation image over a wider range than just one of the detection faces.

In order to achieve the above object, a radiation image capture system according to an aspect of the present invention includes a radiation image capture device configured to perform radiation image capture, and the image-processing device according to an aspect of the present invention configured to add an assist line image to a radiation image captured by the radiation image capture device.

The embodiments of the present invention enable provision of an image-processing device capable of displaying an assist line for assisting observation of a site of interest in a suitable position in a radiation image, and of a radiation image capture system, an image-processing method, and a computer-readable storage medium of the same.

What is claimed is:

1. An image-processing device comprising a processor, the processor being configured to:
    acquire a radiation image of an imaging subject captured by a radiation image capture device for radiographic imaging;
    acquire body thickness information indicating a body thickness of the imaging subject in a direction in which radiation passes through;
    determine a position inside the imaging subject depending on an imaging site of the imaging subject based on the body thickness information; and
    add to the radiation image an assist line image that would be expected to be obtained if a predetermined member had been disposed and captured at the determined position inside the imaging subject.

2. The image-processing device of claim 1, the processor being further configured to add, to the radiation image, information indicating the size of the imaging subject at the position determined based on the body thickness information.

3. The image-processing device of claim 2, wherein the information indicating the size of the imaging subject is a skin line of the imaging subject.

4. An image-processing device comprising a processor, the processor being configured to:
    acquire a radiation image of an imaging subject captured by a radiation image capture device for radiographic imaging;
    acquire body thickness information indicating a body thickness of the imaging subject in a direction in which radiation passes through;
    add to the radiation image an assist line image that would be expected to be obtained if a predetermined member had been disposed and captured at a position inside the imaging subject determined based on the body thickness information, or at a position between the imaging subject and the radiation image capture device;

receive information indicating a change to the position inside the imaging subject and information indicating the position inside the imaging subject after the change; and in cases in which the information indicating the change has been received, change the assist line image added to the radiation image to an assist line image that would be expected to be obtained if the member had been disposed and captured at the position inside the imaging subject after the change.

5. An image-processing device comprising a processor, the processor being configured to:

acquire a radiation image of an imaging subject captured by a radiation image capture device for radiographic imaging;

acquire body thickness information indicating a body thickness of the imaging subject in a direction in which radiation passes through; and add to the radiation image an assist line image that would be expected to be obtained if a predetermined member had been disposed and captured at a position inside the imaging subject determined based on the body thickness information, or at a position between the imaging subject and the radiation image capture device; wherein the body thickness information is information indicating a body thickness of the imaging subject estimated by acquiring imaging conditions of the radiation image, and is based on properties of a virtual grid virtually applied to remove scattered radiation during capturing of the radiation image as virtual grid properties to set a removal amount for scattered radiation, and based on the imaging conditions.

6. The image-processing device of claim 1, wherein the body thickness information is information indicating a body thickness of the imaging subject estimated based on information relating to at least one from out of the age, gender, or build of the imaging subject.

7. The image-processing device of claim 1, wherein the processor is further configured to add the assist line image to the radiation image corrected according to a position of a region of the imaging subject irradiated by the radiation, and a position of a radiation source that radiates the radiation.

8. A radiation image capture system comprising:
a radiation image capture device configured to perform radiation image capture; and
the image-processing device of claim 1 configured to add an assist line image to a radiation image captured by the radiation image capture device.

9. A radiation image capture system comprising:
a radiation image capture device configured to perform radiation image capture; and
an image-processing device comprising a processor, the processor being configured to:
acquire a radiation image of an imaging subject captured by a radiation image capture device for radiographic imaging;
acquire body thickness information indicating a body thickness of the imaging subject in a direction in which radiation passes through; and
add to the radiation image an assist line image that would be expected to be obtained if a predetermined member had been disposed and captured at a position inside the imaging subject determined based on the body thickness information, or at a position between the imaging subject and the radiation image capture device; wherein
the radiation image capture device is a radiation image capture device used for long-length imaging.

10. A radiation image capture system comprising:
a radiation image capture device configured to perform radiation image capture; and
an image-processing device comprising a processor, the processor being configured to:
acquire a radiation image of an imaging subject captured by a radiation image capture device for radiographic imaging;
acquire body thickness information indicating a body thickness of the imaging subject in a direction in which radiation passes through; and
add to the radiation image an assist line image that would be expected to be obtained if a predetermined member had been disposed and captured at a position inside the imaging subject determined based on the body thickness information, or at a position between the imaging subject and the radiation image capture device; wherein
a plurality of radiation detectors that each include a detection face configured to detect radiation are disposed in the radiation image capture device with their detection faces in a state arranged to capture a radiation image over a wider range than just one of the detection faces.

11. An image-processing method, comprising causing a computer to execute processing including:
acquiring a radiation image of an imaging subject captured by a radiation image capture device for radiographic imaging;
acquiring body thickness information indicating a body thickness of the imaging subject in a direction in which radiation passes through;
determining a position inside the imaging subject depending on an imaging site of the imaging subject based on the body thickness information; and
adding to the radiation image an assist line image that would be expected to be obtained if a predetermined member had been disposed and captured at the determined position inside the imaging subject.

12. A non-transitory computer-readable storage medium storing an image-processing program executable by a computer to perform processing including:
acquiring a radiation image of an imaging subject captured by a radiation image capture device for radiographic imaging;
acquiring body thickness information indicating a body thickness of the imaging subject in a direction in which radiation passes through;
determining a position inside the imaging subject depending on an imaging site of the imaging subject based on the body thickness information; and
adding to the radiation image an assist line image that would be expected to be obtained if a predetermined member had been disposed and captured at the determined position inside the imaging subject.

* * * * *